United States Patent
Kulach et al.

(10) Patent No.: US 10,172,533 B2
(45) Date of Patent: Jan. 8, 2019

(54) SWIMMING HEART RATE MONITOR

(71) Applicant: Garmin Switzerland GmbH, Schaffhausen (CH)

(72) Inventors: Christopher J. Kulach, Calgary (CA); Timothy Vandermeiden, Calgary (CA); James K. Rooney, Cochrane (CA); Rogelio A. Rivas, Cochrane (CA); Phillip J. C. Spanswick, Calgary (CA)

(73) Assignee: Garmin Switzerland GmbH (CH)

( * ) Notice: Subject to any disclaimer, the term of this patent is extended or adjusted under 35 U.S.C. 154(b) by 949 days.

(21) Appl. No.: 14/273,241

(22) Filed: May 8, 2014

(65) Prior Publication Data
US 2014/0336493 A1    Nov. 13, 2014

Related U.S. Application Data

(60) Provisional application No. 61/821,403, filed on May 9, 2013, provisional application No. 61/924,275, filed on Jan. 7, 2014.

(51) Int. Cl.
*A61B 5/04* (2006.01)
*A61B 5/0408* (2006.01)
(Continued)

(52) U.S. Cl.
CPC ........ *A61B 5/04085* (2013.01); *A61B 5/0245* (2013.01); *A61B 5/6831* (2013.01); *A61B 5/6823* (2013.01)

(58) Field of Classification Search
CPC ............ A61B 5/04085; A61B 5/04012; A61B 5/0006; A61B 5/0402; A61B 5/681;
(Continued)

(56) References Cited

U.S. PATENT DOCUMENTS 4,691,924 A * 9/1987 Strong ............... A63B 69/0059
273/DIG. 30
4,889,131 A * 12/1989 Salem .................. A61B 5/0006
128/903
(Continued)

FOREIGN PATENT DOCUMENTS

EP         1166713 A1    1/2002
WO    WO 10083441 A1    7/2011

OTHER PUBLICATIONS

Printout from https://buy.garmin.com/en-US/US/shop-by-accessories/fitness-sensors/soft-strap-premium-heart-rate-monitor/prod15490.html , published prior to May 8, 2014.
(Continued)

*Primary Examiner* — Joseph Stoklosa
*Assistant Examiner* — Brian M Antiskay
(74) *Attorney, Agent, or Firm* — Samuel M. Korte; Max M. Ali

(57) ABSTRACT

A swimming heart rate monitor comprises a strap, a first electrode, a second electrode, a first electrical connector, an electronics module, a second electrical connector, and a water sealing feature. The strap covers a portion of a user's chest. The first and second electrodes are positioned on an inner surface of the strap to contact the user's skin. The electrodes provide an electronic heart signal corresponding to the heartbeat of the user. The first electrical connector is positioned on an outer surface of the strap and is in electronic communication with the first and second electrodes. The electronics module may attach to the strap and process the heart signal. The second electrical connector is accessed on the electronics module and may electrically connect to the first electrical connector. The water sealing feature prevents water from interfering with the connection of the first electrical connector and the second electrical connector.

22 Claims, 16 Drawing Sheets

(51) Int. Cl.
*A61B 5/00* (2006.01)
*A61B 5/0245* (2006.01)

(58) Field of Classification Search
CPC . A61B 5/02438; A61B 5/0408; A61B 5/6804; A61B 5/6831
USPC ......... 600/372, 382, 386–391, 393, 508–509
See application file for complete search history.

(56) References Cited

U.S. PATENT DOCUMENTS

| | | | | |
|---|---|---|---|---|
| 6,086,379 | A | 7/2000 | Pendergast et al. | 434/254 |
| 6,580,943 | B2 | 6/2003 | Nissilä | 600/509 |
| 6,955,542 | B2 | 10/2005 | Roncalez et al. | 434/254 |
| 7,310,549 | B1 | 12/2007 | Angelini et al. | 600/509 |
| 7,620,520 | B2 * | 11/2009 | Vock | A43B 3/00 324/109 |
| 2007/0249952 | A1 | 10/2007 | Rubin et al. | 600/544 |
| 2008/0139953 | A1 * | 6/2008 | Baker | A61B 5/0006 600/509 |
| 2011/0172549 | A1 * | 7/2011 | Wijesiriwardana | A61B 5/02438 600/509 |
| 2013/0096411 | A1 * | 4/2013 | Kato | A61B 5/04085 600/390 |
| 2013/0131460 | A1 * | 5/2013 | Yuen | A61B 5/04085 600/301 |
| 2014/0189928 | A1 * | 7/2014 | Oleson | A61B 5/6823 2/69 |

OTHER PUBLICATIONS

Printout from http://www.dcrainmaker.com/2014/07/suunto-ambit3-multisport.html , p. 7, published prior to May 8, 2014.
Printout from http://www.polar.com/ca-en/products/accessories/T31_coded_Transmitter, published prior to May 8, 2014.
Printout from http://www.suunto.com/Products/Heart-Rate-Belts/Suunto-Memory-Belt/, published prior to May 8, 2014.
Printout from http://www.finisinc.com/Aqua-Puise_2 , published prior to May 8, 2014.
Printout from http://www.swimovate.com/poolmatehr/ , published prior to May 8, 2014.
Annex to form PCT/ISA/206 Communication Relating to the Results of the Partial International Search for PCT/IB2014/001315 filed May 8, 2014.

* cited by examiner

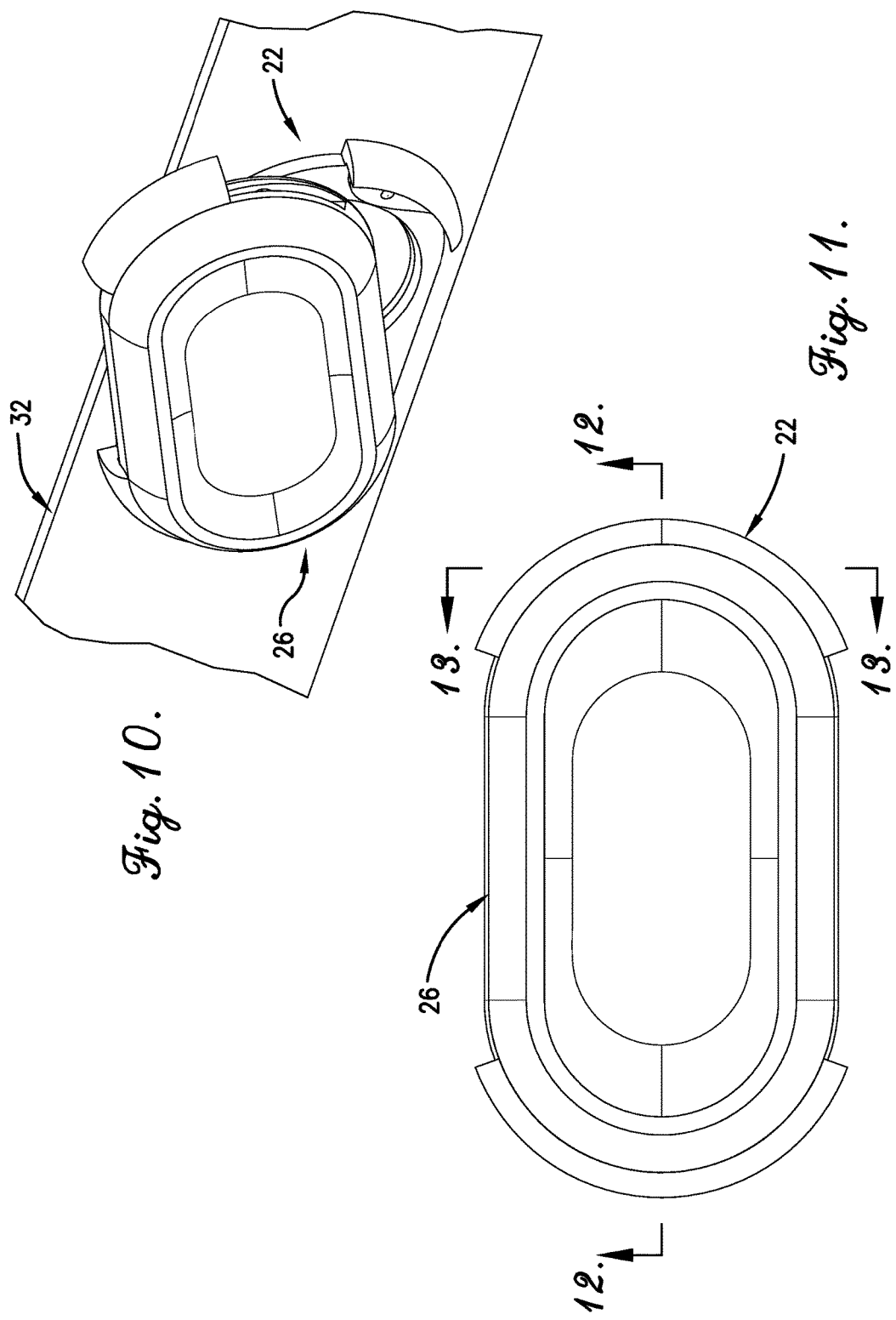

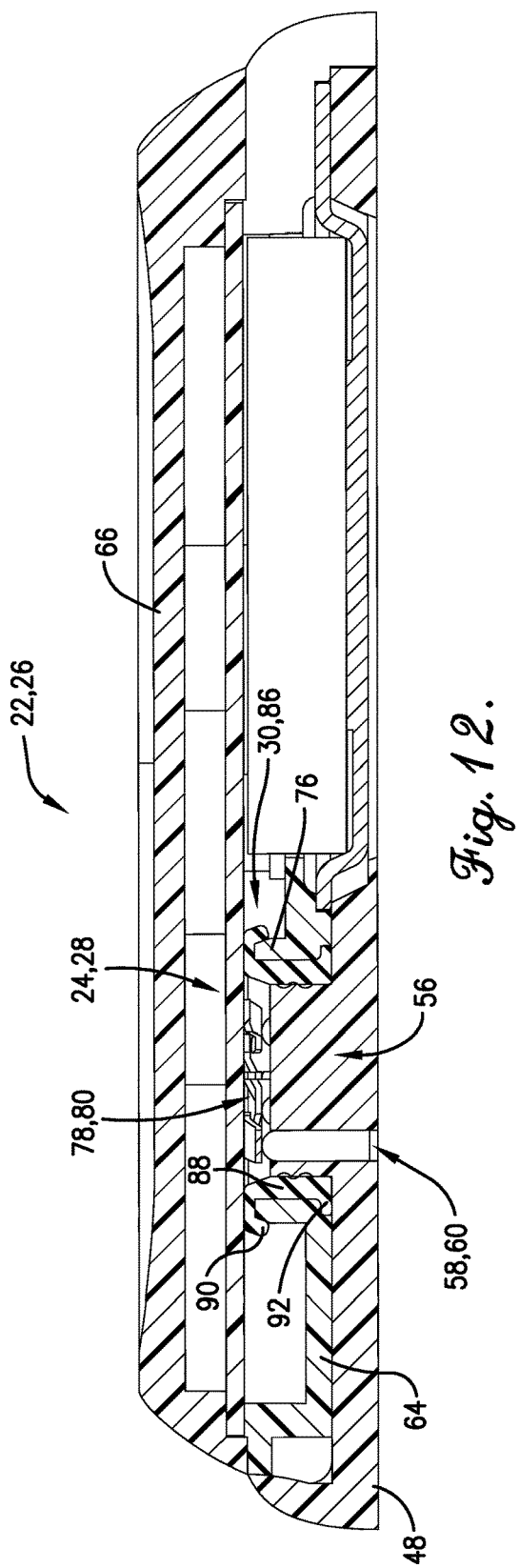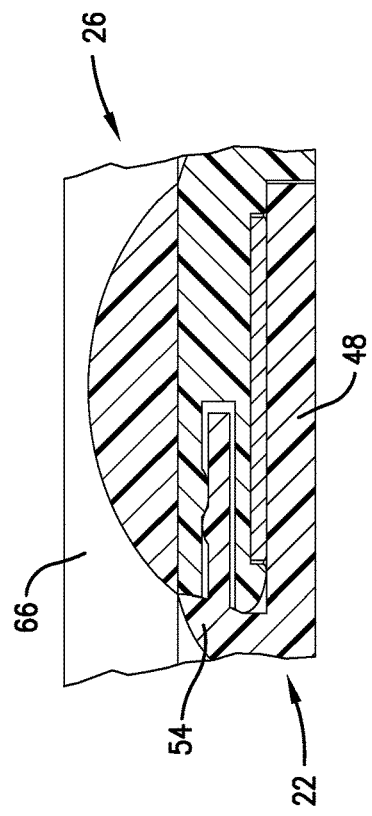

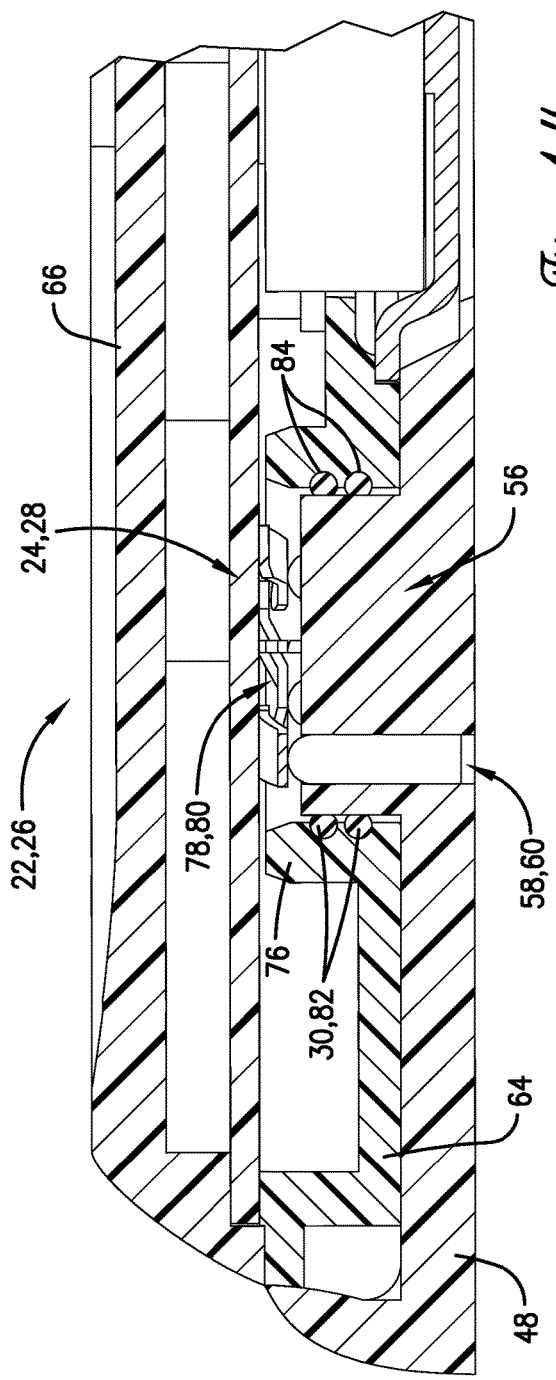
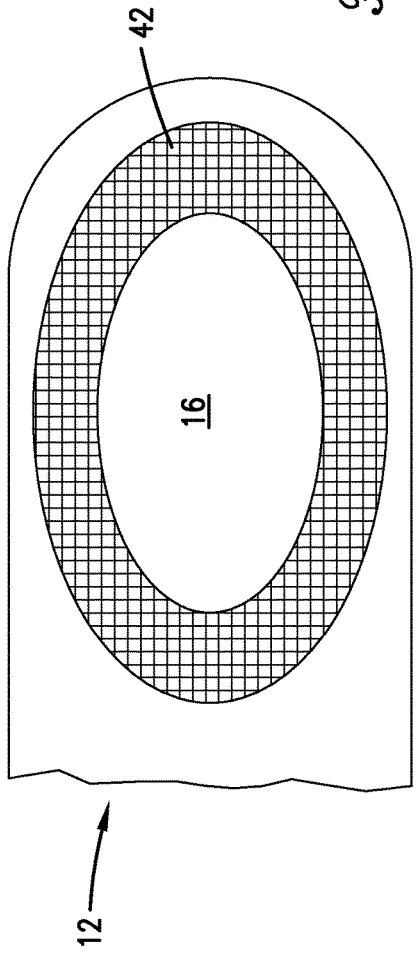

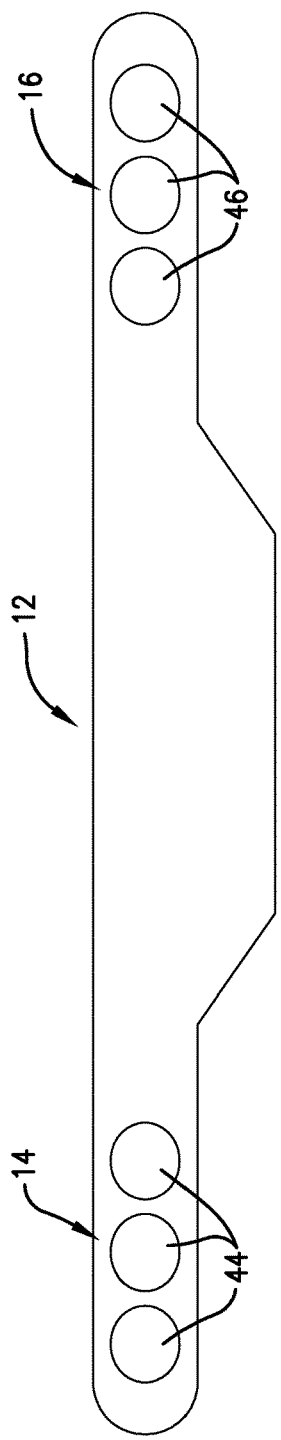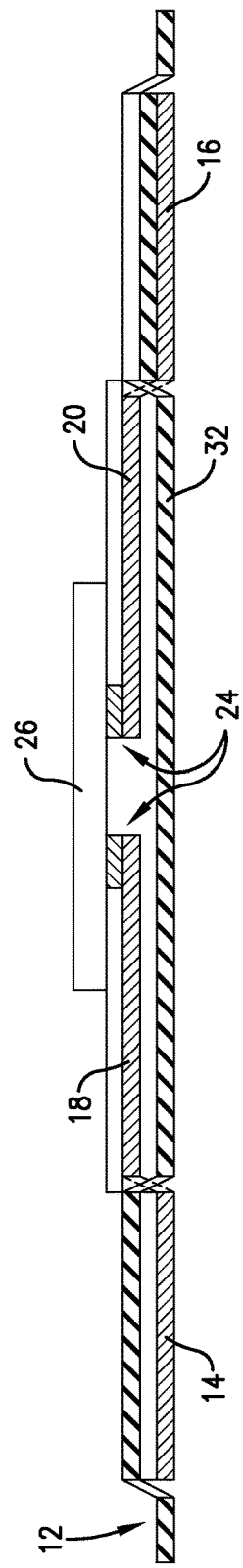

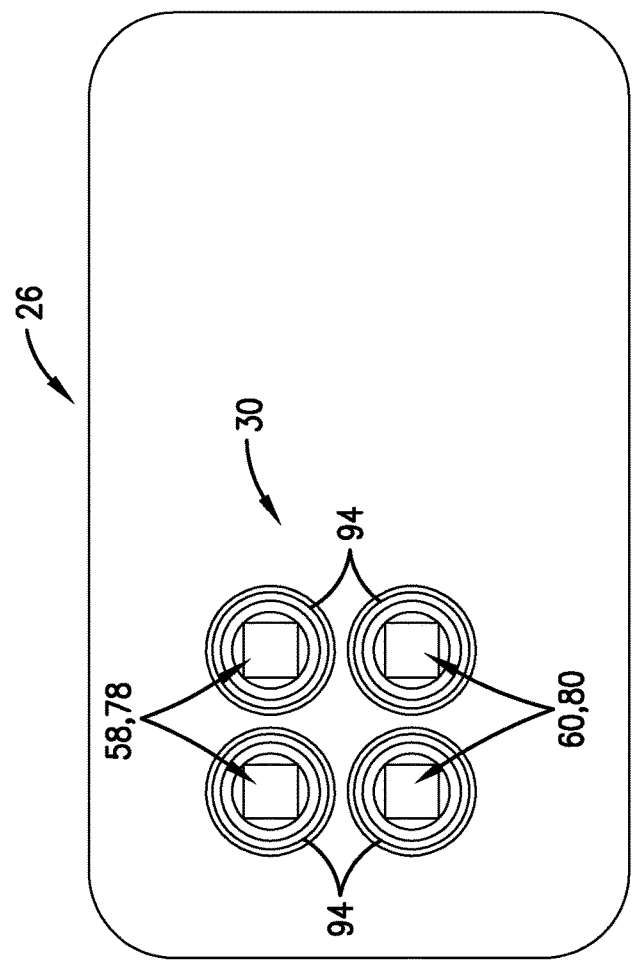

SWIMMING HEART RATE MONITOR

RELATED APPLICATIONS

The current non-provisional patent application claims priority benefit, with regard to all common subject matter, of an earlier-filed U.S. provisional patent application titled "HEART RATE MONITOR (HRM) WITH INERTIAL SENSING", Application Ser. No. 61/821,403, filed May 9, 2013, and U.S. provisional patent application titled "HEART RATE MONITOR (HRM) WITH INERTIAL SENSING", Application Ser. No. 61/924,275, filed Jan. 7, 2014. These earlier-filed applications are hereby incorporated by reference into the current application in their entirety.

BACKGROUND

Athletes often wear a heart rate monitor in order to help them regulate their physical motions while doing physical activity to maintain an optimal heart rate level by monitoring a current heart rate. The heart rate monitor typically includes an electronics module that determines the user's heart rate based on an electronic signal received from a pair of electrodes that contact the user's skin. The electronics module is typically coupled with electrodes that are attached to or embedded in an adjustable strap that is worn around the user's chest to determine the user's heart rate while the user engages in physical activity. Typically, the conventional adjustable straps include an elastic section that adjusts to provide the majority of the total length of the strap when worn. Conventional heart rate monitors are primarily used in dry conditions but may be subjected to fluids, such as perspiration and drinking water. When used for swimming this environment becomes more challenging with chlorinated water, salt water and body movement all in a higher pressure environment.

SUMMARY

The straps of conventional heart rate monitor systems may be tightened and adjusted to fit the user's torso, but the straps tend to slide down the user's torso from the chest toward the waist during water activities. In addition, the strap may rotate, roll, buckle, or fold over as a result of water flowing around the strap when the user is engaged in water activities. Furthermore, water may severely degrade a path of an electronic heart signal associated with a user's heartbeat that is received from electrodes positioned on an inner surface of the strap and provided to the electronics module, thereby attenuating the electronic signal and reducing the ability of the electronics module to accurately determine a heart rate.

Embodiments of the present technology provide a swimming heart rate monitor that at least partially alleviates these problems. An embodiment of the swimming heart rate monitor broadly comprises a strap, a first electrode, a second electrode, a module coupler, a first electrical connector, an electronics module, a second electrical connector, and a water sealing feature.

The strap may include a substantially elastic section having a first length configured to stretch when the strap is worn and a substantially inelastic section having a second length positioned at least partially in a front portion of the strap and configured to cover at least a portion of a user's chest. The second length may be twice the first length. The first and second electrodes may be spaced apart from one another and positioned on an inner surface of the substantially inelastic section. The electrodes may also contact the user's skin and provide an electronic heart signal corresponding to the heartbeat of the user. An electrical connector positioned on an outer surface of the first substantially inelastic section may be in electronic contact with the first and second electrodes.

The module coupler may be positioned on an outer surface of the strap and may include a first mating feature. The first electrical connector may be in electrical contact with the first and second electrodes and may be retained on the module coupler. The first electrical connector may include a post that encloses a plurality of electrical contacts.

The electronics module may process the heart signal provided by the first and second electrodes and may include a housing with an upper wall and an opposing lower wall. In addition, the housing may include a second mating feature configured to mate with the first mating feature so as to retain the electronics module. The second electrical connector may be positioned on an outer surface of the electronics module and configured to electrically connect to the first electrical connector.

The water sealing feature prevents water from accessing the connection of the first electrical connector and the second electrical connector when the electronics module is attached to the module coupler and submerged in water. The water sealing feature may include first and second O-rings axially spaced and positioned on a post of the electrical connector. The water sealing feature may include a cylindrical shaped water seal with a circumferential sidewall, an upper collar, and a lower flange. The water sealing feature may include a plurality of seals between the module coupler and the electronics module. The substantially inelastic section may be coated along an inner surface with a material to increase a coefficient of static friction between the strap and the user's skin.

The substantially inelastic section may include an adjustable substantially inelastic section that is positioned in a back portion of the strap configured to adjust a total length of the strap. The substantially elastic section may comprise a first elastic section and a second substantially elastic section. The center of the second substantially elastic section and the center of the first substantially elastic section may be spaced approximately 180 degrees apart along a circumference of the strap separated by a portion of the substantially inelastic section. One or more inelastic sections may be positioned between the first elastic section and the second substantially elastic section.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present technology will be apparent from the following detailed description of the embodiments and the accompanying drawing figures.

BRIEF DESCRIPTION OF THE DRAWING FIGURES

Embodiments of the present technology are described in detail below with reference to the attached drawing figures, wherein:

FIG. 10 is a front perspective view of the electronics module partially attached to the module coupler;

FIG. 11 is a top view of the electronics module attached to the module coupler;

FIG. 12 is a sectional view of the electronics module cut along the line 12-12 of FIG. 11, depicting a first embodiment of a water sealing feature;

FIG. 13 is a fragmentary sectional view of the electronics module cut along the line 13-13 of FIG. 11;

FIG. 14 is a fragmentary sectional view of the electronics module cut along the line 12-12 of FIG. 11, depicting a second embodiment of the water sealing feature;

FIG. 15 is a fragmentary front view of a first electrode;

FIG. 16 is a top view of a portion of the strap including a plurality first electrodes and a plurality of second electrodes;

FIG. 17 is a sectional view of a portion of the strap, a first electrode, a second electrode, a first electrode conductor, a second electrode conductor, and the electronics module;

FIG. 18 is a schematic view of alternative embodiments of the first electrical connector, the second electrical connector, and the water sealing element;

Figure 1:
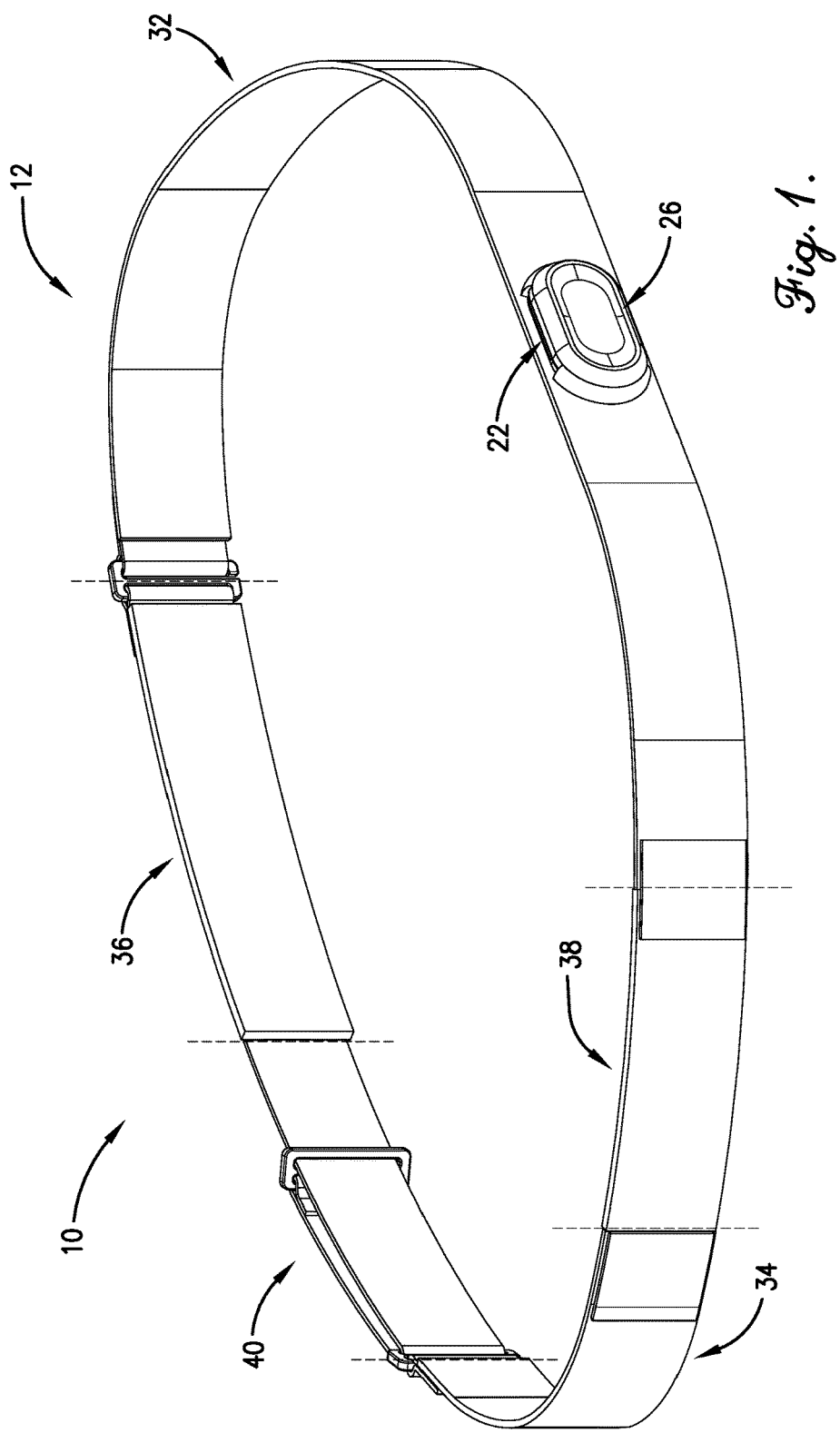
FIG. 1 is a front perspective view of a swimming heart rate monitor constructed in accordance with various embodiments of the current technology, the swimming heart rate monitor including a first embodiment of a strap and an electronics module attached thereto.
Figure 2:
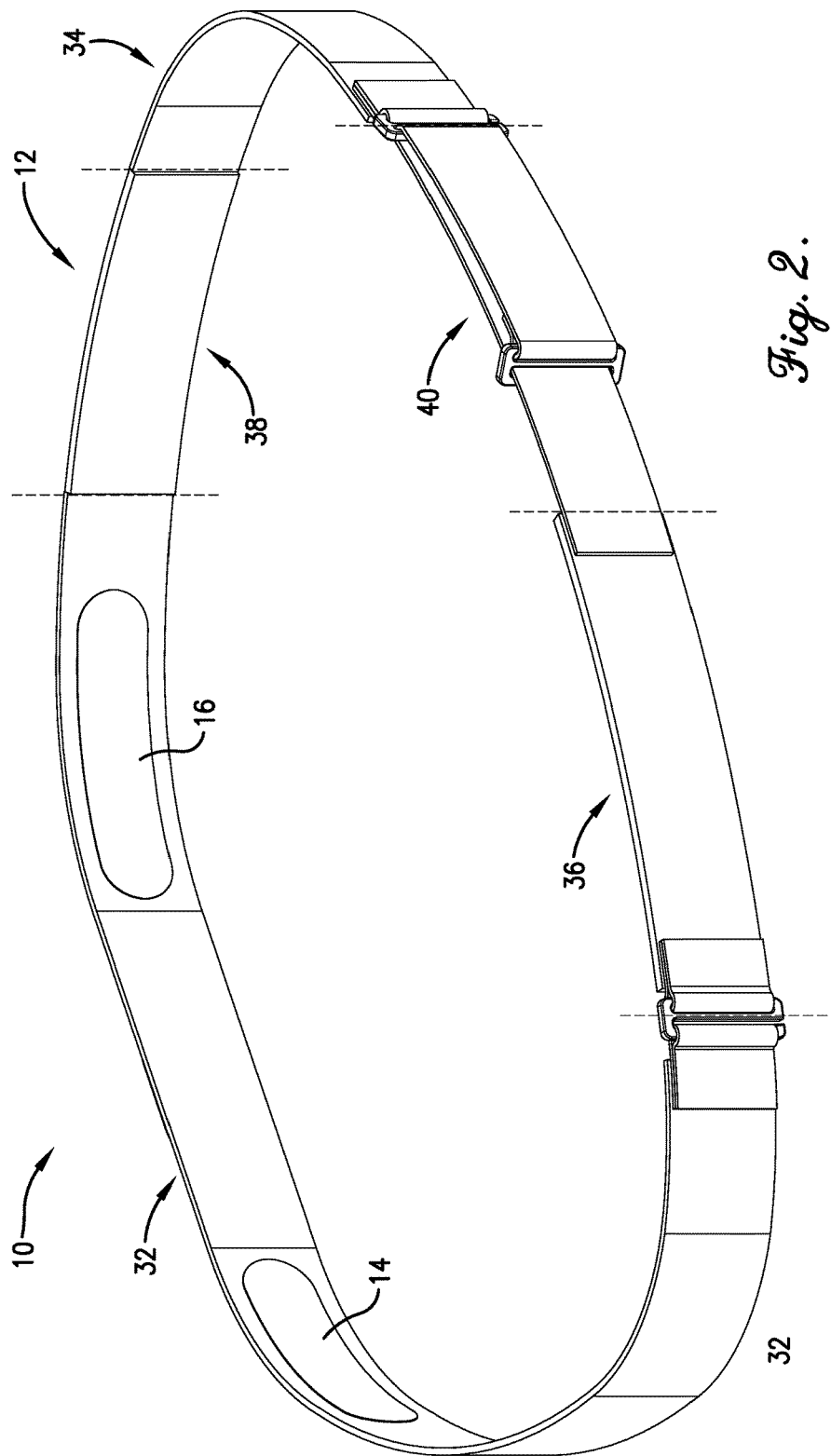
FIG. 2 is a rear perspective view of the swimming heart rate monitor including first and second electrodes.
Figure 3:
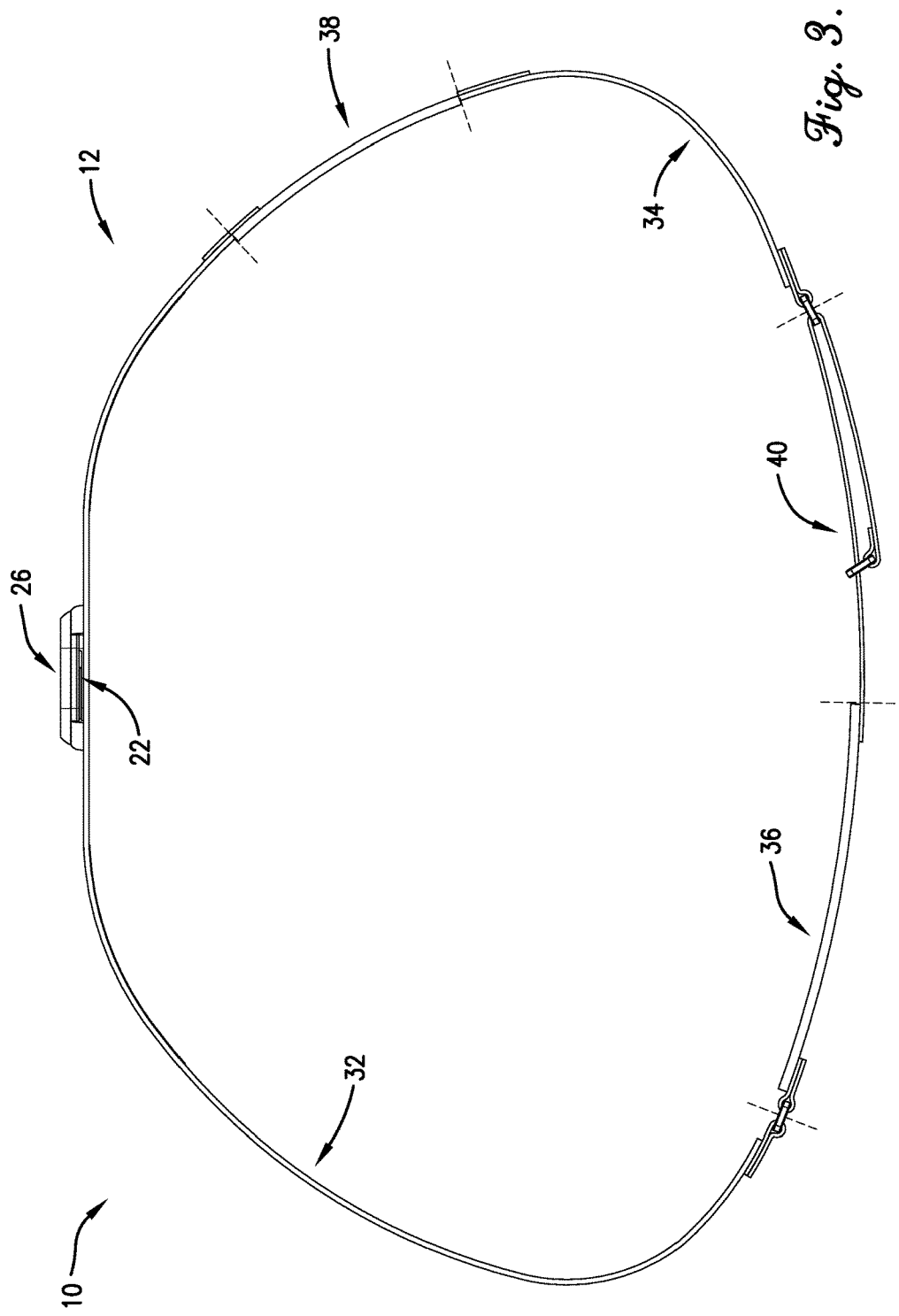
FIG. 3 is a top view of the swimming heart rate monitor.

The drawing figures do not limit the present technology to the specific embodiments disclosed and described herein. The drawings are not necessarily to scale, emphasis instead being placed upon clearly illustrating the principles of the technology.

DETAILED DESCRIPTION

The following detailed description of the technology references the accompanying drawings that illustrate specific embodiments in which the technology can be practiced. The embodiments are intended to describe aspects of the technology in sufficient detail to enable those skilled in the art to practice the technology. Other embodiments can be utilized and changes can be made without departing from the scope of the present technology. The following detailed description is, therefore, not to be taken in a limiting sense. The scope of the present technology is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Embodiments of the present technology relate to a heart rate monitor for use while engaged in water activities, such as swimming. A user's heart beat generates electrical activity within the user's body. Two or more electrodes positioned on the user's skin, with at least one being in the vicinity of the heart can detect a cardiac biopotential difference resulting from the electrical activity of the heart. An electronic heart signal corresponding to the cardiac biopotential difference is processed to determine the user's heart rate. The user may monitor his heart while engaged in the water activity or review heart rate data after completion of the water activity.

The heart rate monitor may include an electronics module with electronic components for processing the heart signal, a pair of electrodes for generating the heart signal, and a strap. The electronics module may be attached to an outer surface of the strap, while the electrodes are retained on an inner surface of the strap. An electrode conductor may be positioned between an inner and outer surface of the strap to electrically connect the electrode positioned on an inner surface of the strap to an electrical connector positioned on an outer surface of the strap. The strap is generally worn high on the user's torso, just below the chest, so that the electrodes can contact the user's skin in the vicinity of the heart. This positioning usually provides the optimal position on a user torso to sense the user's heart rate because it provides high amplitude of the heart signal from the electrodes, resulting in accurate determination of the user's heart rate.

Conventional chest worn straps are adjustable and mostly elastic to provide the most comfort for users because the straps may be sufficiently tightened to stay in place during substantially dry conditions while providing an amount of strap expansion that does not hinder the user's breathing. The adjustable portion of many conventional straps is elastic as well. The elastic portions of conventional straps may be adjusted for use during strenuous physical exercise and medical cardiovascular uses by users having varying chest sizes. For example, conventional straps may be adjusted to a maximum total length such that the inelastic portion comprises a very small portion of the total length, such as 20% of the total length, and the elastic portion comprises the bulk of the total length, such as 80% of the total length.

If the conventional straps has sections or is constructed using a material that is too elastic or has a low coefficient of static friction against the skin of the user's torso, then the strap may gradually slide or slip down the user's torso away from the heart region while the user is swimming, which may result in the amplitude of the heart signal decreasing as the strap slides away from the heart. As a result, the ability of the electronics module to determine the user's heart may diminish when the strap slides down the torso. Furthermore, having the strap rotate or slide may become a nuisance because the user has to repeatedly reposition the strap in the optimal position for the electrodes to sense the user's heart rate.

The predominantly-elastic, conventional straps may be tightened and subjected to fluids, such as perspiration and drinking water, but the conventional straps may fail to adequately prevent water from passing between the strap and the user's skin as water flows around the strap, resulting in loss of contact between the electrodes and the skin and, consequently, a low-quality heart signal. In this event, the electronics module of the conventional strap cannot determine the heart rate of the user because the electrodes are not secured against the user's torso. Excessively elastic conventional straps may also rotate, roll, buckle, or fold over while the user is swimming. If the strap folds over in the region where the electrodes are located, then the electrodes may lose contact with the surface of the skin, thereby unable to sense the heart signal. Thus, the conventional configuration of maximizing the elastic portions of adjustable straps may be very comfortable for users and suitable for use of the straps in dry conditions, when the straps are exposed to perspiration and drinking water, but the conventional configuration is not adequate for water activities.

The electronics module may be integrated with the strap or removably attached to the strap. Thus, for electronics modules that are removably attached to the strap, there is an interface between the electronics module and the strap that includes an electrical connector on the strap with first and second contacts, which provide the heart signal provided by the first and second electrodes, and an electrical connector on the electronics module with first and second contacts, which receive the heart signal provided by the electrodes when the electrical connectors are electrically coupled. In embodiments, the first electrical contact of the strap includes a post on the outer surface of the strap that encloses the first and second contacts. In embodiments, a module coupler is positioned on the outer surface of the strap to secure the electronics module to the strap by using a mating feature. The electronics module may be attached to the strap to provide mechanical and electrical coupling when the electronics module is removably connected to the strap. Mechanical coupling between the electronics module and strap may secure the electrical module to the user's torso and electrical coupling may be enabled by the use of conductive materials that allow an electrical signal to be communicated between the electronics module and strap.

A removable electronics module may be attached to more than one strap. Thus, a user may have more than one strap, and use the same electronics module with the multiple straps. In one embodiment, separate straps may be used in and out of water, and one electronics module may attach to and be used with both straps. In this embodiment, the strap to be used mostly in water is optimized for the water environment as detailed below and the second strap, to be used mostly out of water, is optimized for comfort and performance for the dry, on-land environment. Thus, the ability to share the electronics module between different straps allows for achieving optimum performance with minimal system cost increase as a result of the techniques disclosed herein. In one embodiment, one electronics module and multiple straps for use in the same environment are provided. In this embodiment, the user is able to use a different strap for several consecutive workouts, and wash the multiple straps together periodically. Thus, the user has access to a fresh strap for each workout without having to replace the electronics module for the different environments.

When the electronics module is attached to the strap, the first contact of the strap electrical connector physically touches the first contact of the electronics module electrical connector, and the second contact of the strap electrical connector touches the second contact of the electronics module electrical connector. In conventional heart rate monitors, neither electrical connector has an adequate water seal to prevent water from interfering with the electrical signal by entering and forming a conductive path between the first and second contacts of the electrical connectors when the conventional electronics module is attached to the conventional strap. As a result, the amplitude of the heart signal may be attenuated and the ability of the electronics module to determine the user's heart rate may be diminished by an unsealed electrical connection in conventional heart rate monitors.

Embodiments of the technology will now be described in more detail with reference to the drawing figures. Referring initially to FIGS. 1-3, 5-9, and 17 a heart rate monitor 10 for use while swimming is illustrated. The heart rate monitor 10 may broadly comprise a strap 12, a first electrode 14, a second electrode 16, a first electrode conductor 18, a second electrode conductor 20, a module coupler 22, a first electrical connector 24, an electronics module 26, a second electrical connector 28, and a water sealing feature 30.

The heart rate monitor 10 is generally worn on the upper torso of a user, such that a portion of the strap 12 is positioned just below the user's chest in the vicinity of the heart in order to detect a cardiac biopotential that is processed to determine the user's heart rate. The strap 12 includes features that reduce the possibility of the strap 12 rotating, sliding, rolling, buckling, or folding over that may result from forces caused by the water while the user engages in water activities, such as swimming. Furthermore, the water sealing feature 30 reduces the possibility of attenuating or losing the heart signal due to water interfering with the electronic heart signal by entering and forming a conductive path between contacts of the first electrical connector 24 and/or the second electrical connector 28.

The improvements detailed herein enable the strap 12 to hold the first electrode 14 and the second electrode 16 in place against the surface of the skin of the user while engaged in water activities. The strap 12 is also mechanically and electrically coupled with the electronics module 26. The strap 12 may include a substantially elastic section having a first length configured to stretch when the strap is worn and a substantially inelastic section having a second length positioned at least partially in a front portion of the strap and configured to cover at least a portion of a user's chest. In embodiments, the second length may be at least twice the first length. However, it is to be understood that some benefits achieved by applying the techniques disclosed herein may be obtained by using a strap having a second length that is less than twice the first length. In embodiments, the substantially elastic section stretches to a maximum third length that is larger than the first length and does not increase as the total length of the strap increases. For example, the substantially elastic section of the strap may have a first length that is the smallest possible length for the substantially elastic section, such as before the strap is worn, and a maximum third length that may be achieved for users having the largest chest size. The substantially elastic section of the strap may stretch to a length between the first length and the third length for users having an intermediate chest size.

The substantially elastic section may include a first substantially elastic section and a second substantially elastic section. The first substantially elastic section may be separated from the second substantially elastic section and have one or more inelastic sections between the first substantially elastic section and the second substantially elastic section. For example, a center of the first substantially elastic section and a center of the second substantially elastic section spaced may be approximately 180 degrees apart along a circumference of the strap. In some embodiments, the first substantially elastic section is offset to one side of the strap. For example, substantially inelastic section of the strap may be positioned at the center near the user's sternum and the first substantially elastic section may be offset 40 to 65 degrees from the center. This offset first substantially elastic section may enable the strap to sufficiently expand to enable unobstructed breathing by the user and the substantially inelastic section positioned at the center may include a first electrical connector positioned on an outer surface of the strap and the first electrode and a second electrode spaced apart from one another and positioned on an inner surface of the strap.

The first electrical connector may be positioned on an outer surface of the strap and may be enclosed by a water sealing feature. The water sealing feature may include first and second O-rings axially spaced and positioned on a post of the electrical connector, a cylindrical shaped water seal with a circumferential sidewall, an upper collar, and a lower flange, or a plurality of seals between a module coupler on an outer surface of the strap and an electronics module, or any combination thereof. As detailed herein, this water sealing feature prevents water from interfering with the electronic heart signal between the first electrical connector and a second electrical connector, which is accessed on the lower wall of the electronics module housing and configured to electrically connect to the first electrical connector, when the electronics module is attached to the strap and submerged in water.

The substantially inelastic section may include an adjustable substantially inelastic section positioned in a back portion of the strap configured to adjust a total length of the strap. The adjustable substantially inelastic section may be separated from other substantially inelastic sections and have one or more elastic sections between the adjustable substantially inelastic section and other substantially inelastic sections.

An embodiment of the strap 12, as shown in FIGS. 1-4, may include a first substantially inelastic section 32, a second substantially inelastic section 34, a first substantially elastic section 36, a second substantially elastic section 38, and an adjustable substantially inelastic section 40. The first substantially inelastic section 32, as seen in FIGS. 1-4, may have an elongated band shape with an inner surface configured to contact the user's skin and an opposing outer surface that does not contact the skin. In embodiments, the inner surface is corrugated to increase resistance between the strap 12 and the user's skin. In other embodiments, the inner surface is flat and smooth, and utilizes other properties of the material, such as fiber features at micro or nano scale to increase resistance between the strap 12 and the user's skin. An exemplary first substantially inelastic section 32 may have a width ranging from approximately 2 centimeters (cm) to approximately 5 cm and a length ranging from approximately 60 cm to approximately 80 cm.

In some embodiments, the first substantially inelastic section 32 may be formed from a flexible material with a lower degree of elasticity than the first and second substantially elastic sections 34, 36 such that the first substantially inelastic section 32 does not appreciably stretch or otherwise change shape when it is wet or dry. An exemplary material for the first substantially inelastic section 32 may include a satin-woven fabric made with a synthetic fiber, such as polyester. Generally, the material for the first substantially inelastic section 32 has a high coefficient of static friction against skin when wet, and enough structure to maintain its shape but flexible enough to maintain contact with the surface of the skin. Optionally, a thin layer or coating of a substance, such as silicone or nitrile rubber, may be applied to the inner surface of one or portions of strap 12, such as the first substantially inelastic section 32, to increase the coefficient of static friction of the strap 12 against the user's skin to reduce any rotation or sliding as a result of water flowing around the strap 12. In some embodiments, the substance may be applied to the inner surface of strap 12 in a smooth, continuous fashion so that the coating of the substance is uniform. In other embodiments, the substance may be applied to the inner surface of strap 12 in a pattern such that some areas of the inner surface are coated while other areas are not. The pattern may allow for at least partial breathability of the skin under the first and second substantially inelastic sections 32, 34 or other strap sections. In various embodiments, the coating of the substance may have a thickness ranging from approximately 0.05 millimeters (mm) to 1.0 mm.

In other embodiments, the first substantially inelastic section 32 may be formed from a two-layer material having a first, inner layer and a second, outer layer that is in contact with the environment, such as the user's skin and any water around the first substantially inelastic section 32. The first, inner layer may include thin polymers, elastomers, fabric materials, rubber materials, or the like to provide minimal stretching and reduce any rolling, buckling, or folding over of strap 12. The second, outer layer may include a thin semi-elastic material with a high coefficient of static friction against the user's skin when the second layer is wet to reduce any rotation or sliding of strap 12. The second layer may have other properties, such as stretching from approximately 1% to approximately 20% of its length under a tensional force of less than 5 kilograms (kg), to improve the coefficient of friction against the user's skin while retaining durability and comfort. The second layer may be configured as a sheath or a tube within which the first layer is positioned. In some embodiments, the first layer may be attached or secured to the second layer at any position along the length of the first substantially inelastic section 32. In other embodiments, the first layer and the second layer may be in contact but unconnected. In certain embodiments, the second layer may have a thin layer or coating of a substance, such as silicone or nitrile rubber, applied to its outer surface to increase the coefficient of static friction of the first substantially inelastic section 32 against the user's skin.

In still other embodiments, the first substantially inelastic section 32 may be formed from a flexible, low-elasticity material that inherently has a high coefficient of static friction against the user's skin. The material may include microstructures which interact with micro skin features to resist rotating, slipping and peeling. An exemplary material may include nanoFront™.

The second substantially inelastic section 34, as seen in FIGS. 1-4, may be constructed from the same material as the first substantially inelastic section 32 and may have the same width as the first substantially inelastic section 32, but its length may range from approximately 10 cm to approximately 30 cm. In addition, the second substantially inelastic section 34 may have an inner surface and an outer surface, with the inner surface having a frictional coating.

The first substantially elastic section 36 and the second substantially elastic section 38, as seen in FIGS. 1-4, may each be constructed from a flexible material with a higher degree of elasticity than the first and second substantially inelastic sections 32, 24 such that it stretches when a force is applied and returns to its shape when the force is removed. Exemplary materials include fabric elastics, fabric elastics with elastane fibers, polymers, rubbers, or the like. In combination, the first and second substantially elastic sections 36, 38 provide tension to maintain the position of the strap 12 on the user's body while the strap 12 is being worn and the user is breathing. In embodiments, strap 12 may include only the first substantially elastic section 36.

In embodiments, the first substantially elastic section 36 and the second substantially elastic section 38 may each have an elongation of less than 10% at approximately 300 grams (g) of loading force and more than 5% elongation at approximately 2.5 kg of loading force. The first substantially elastic section 36 may include an open-ended hook connector, or similar removable coupler, attached to one end thereof.

The first substantially elastic section 36 and the second substantially elastic section 38 may each have a width approximately the same or less than the width of the first and second substantially inelastic sections 32, 34. The lengths of the first and second substantially elastic sections 36, 38 may vary inversely with the degree of elasticity of the material used to form the sections 36, 38. For example, first and second substantially elastic sections 36, 38 formed from material with greater elasticity may be shorter than first and second substantially elastic sections 36, 38 formed from material with lower elasticity. Exemplary first and second substantially elastic sections 36, 38 may each have a length ranging from approximately 2 cm to approximately 15 cm.

The adjustable substantially inelastic section 40, as seen in FIGS. 1-4, may be constructed from similar material and may have a similar width as the first and second substantially inelastic sections 32, 34. The adjustable substantially inelastic section 40 may include a mechanism or components that adjust or vary the length of the adjustable substantially inelastic section 40. An exemplary adjustable substantially inelastic section 40 may include a band of inelastic material, a double loop slider, and a hook and loop slider to adjust the length of the adjustable substantially inelastic section 40. The band of inelastic material may include a first end and an opposing second end that is coupled to a first loop of the double loop slider. The band of inelastic material may pass through a second loop of the double loop slider. Thus, the second end of the band of inelastic material overlaps the intermediate portion of the band. To adjust the length of the adjustable substantially inelastic section 40, the double loop slider is moved along the intermediate portion of the band of inelastic material to a location that provides the desired total length. In addition, the band of inelastic material may pass through the loop of the hook and loop slider. With this exemplary configuration, a first end of the adjustable substantially inelastic section 40 may be formed by the first end of the band of inelastic material, while a second end of the adjustable substantially inelastic section 40 may be formed by a portion of the hook and loop slider.

The first electrode 14 and the second electrode 16 detect electrical activity of the heart related to the heartbeat and, in combination, generate a heart signal corresponding to the cardiac biopotential difference. The first electrode 14 and the second electrode 16, as seen in FIGS. 2 and 15-17, may each be constructed from electrically conductive material that is flexible and can maintain contact with the skin during water activities. Exemplary materials may include conductive thermoplastic polyurethane (CTPU), conductive silicone, or conductive polymers. The first electrode 14 and the second electrode 16 may be spaced apart and positioned along the inner surface of the strap 12, such as the inner surface of the first substantially inelastic section 32. Each electrode 14, 16 may have a circular, oval, rectangular, or similar shape. In various embodiments shown in FIG. 15, the perimeter of each electrode 14, 16 may be surrounded by a water seal 42 with roughly the same shape thereof. The water seal 42 may include a single ridge outlining the electrode 14, 16 or a plurality of ridges presented in a pattern.

In some embodiments as shown in FIG. 16, the first electrode 14 and the second electrode 16 may each include a plurality of individual electrodes. In an exemplary embodiment, the first electrode 14 may include three individual electrodes 44 and the second electrode 16 may include three individual electrodes 46. Each set of electrodes 44, 46 may be spaced apart from one another either parallel to the longitudinal axis of the strap 12 or transverse to the longitudinal axis. Each individual electrode 44, 46 of the first and second electrodes 14, 16 may provide a heart signal that is received by the electronics module 26 after it passes through the first and second electrode conductors 18, 20, the first electrical connector 24 and the second electrical connector 28. In embodiments, the electronics module 26 may use the heart signal provided by one of the individual electrodes 44, 46 based on signal quality, amplitude, or other criteria to determine the user's heart rate.

The first electrode conductor 18 connects the first electrode 14 to the first electrical connector 24, and the second electrode conductor 20 connects the second electrode 16 to the first electrical connector 24, as seen in FIG. 17. The electrode conductors 18, 20 may be formed from the same material as the first and second electrodes 14, 16 or from a different material. In certain embodiments, the electrode conductors 18, 20 may be formed from electrically conductive wires or cables. Furthermore, in embodiments that include a plurality of first electrodes 44 and a plurality of second electrodes 46, there may a plurality of individual first electrode conductors 18, 20 and a plurality of individual second electrode conductors 18, 20. Generally, there is one first electrode conductor 18 for each first electrode 14 and one second electrode conductor 20 for each second electrode 16.

The electrode conductors 18, 20 may be retained at least within the first substantially inelastic section 32. There may be a pocket in the first substantially inelastic section 32 within which the electrode conductors 18, 20 are positioned. Or, there may be an extra layer of inelastic material placed over the electrode conductors 18, 20 while they are positioned on the inner surface of the first substantially inelastic section 32.

Figure 5:
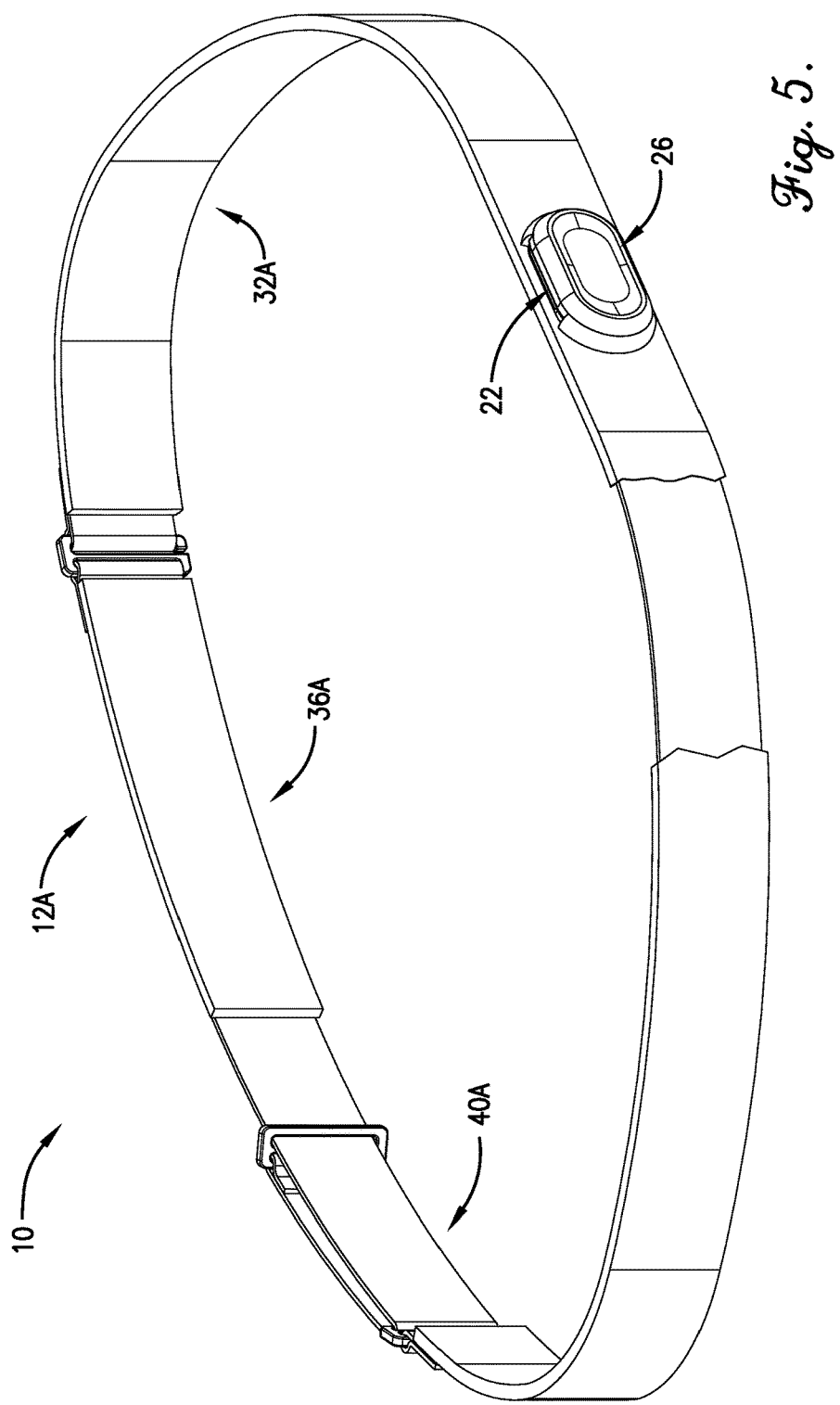
FIG. 5 is a front perspective view of the swimming heart rate monitor including a second embodiment of the strap.
Figure 6:
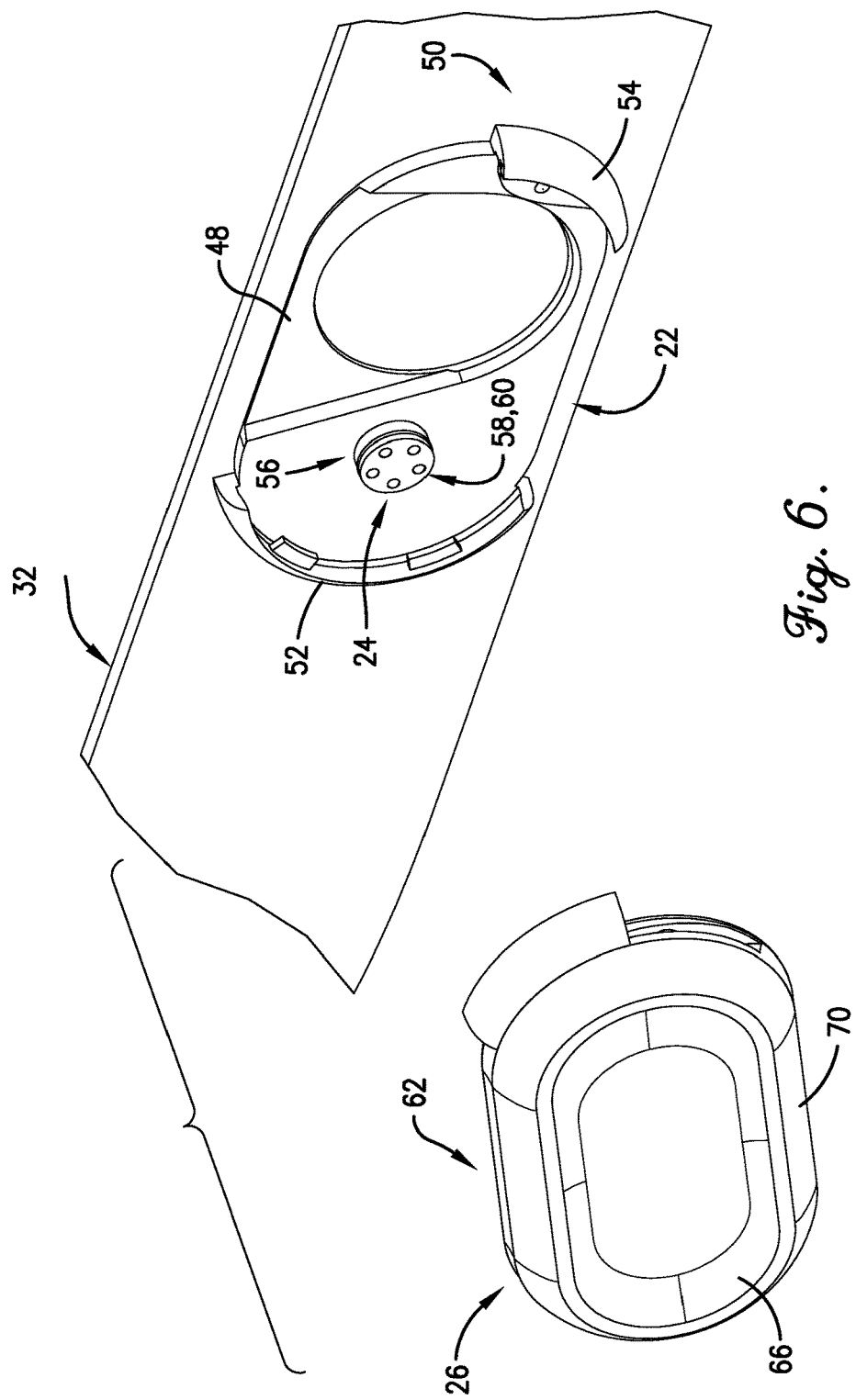
FIG. 6 is a fragmentary front perspective view from a first side of components of the heart rate monitor including a module coupler, a first electrical connector, and an electronics module.

An embodiment of the strap 12 may be configured as follows. As shown in FIG. 5, a strap 12A may include only a first substantially inelastic section 32A, a first substantially elastic section 36A, and an adjustable substantially inelastic section 40A, with each section stitched or removably coupled to the other two to form a single, continuous strap 12 that may be worn around a user's torso. The first substantially inelastic section 32A, the first substantially elastic section 36A, and the adjustable substantially inelastic section 40A may be similar to the first substantially inelastic section 32, the first substantially elastic section 36, and the adjustable substantially inelastic section 40 as described herein. In exemplary configurations, the first substantially inelastic section 32A may be removably coupled to the first substantially elastic section 36A and the adjustable substantially inelastic section 40A. Thus, the strap 12 may comprise three portions that are stitched or removably coupled to adjacent portions to form a single, continuous strap 12 that may be worn around a user's torso. In addition, the first substantially inelastic section 32A may have a length equal to a sum of the lengths of the first substantially inelastic section 32, the second substantially inelastic section 34, and the second substantially elastic section 38 of the strap 12. Furthermore, an exemplary first substantially inelastic section 32A may be formed from semi-elastic material. The strap 12A may be worn such that the first substantially inelastic section 32A covers the user's chest and left and right sides. The first substantially elastic section 36A and the adjustable substantially inelastic section 40A may be positioned along the user's back. In embodiments, the adjustable substantially inelastic section 40A may be positioned at the center of the user's back. In some embodiments, the strap 12 may not include an adjustable substantially inelastic section 40 and may thus rely on the first substantially elastic section 36 to provide the variance in total length of strap 12 to enable a user to comfortably wear strap 12 while swimming.

In one embodiment, the substantially inelastic sections 32, 34 may contain a adjustability feature to adjust the length of strap 12. The adjustability feature may be provided in addition to or lieu of the adjustable substantially inelastic section 40 to provide additional areas to adjust the length of strap 12 or reduce the number of elements forming strap 12.

In other embodiments, as shown in FIGS. 1-4, the electronics module 26 may be positioned along an outer surface of the first substantially inelastic section 32, a first end of the first substantially inelastic section 32 may be coupled with a first end of the second substantially elastic section 38, a second end of the second substantially elastic section 38 may be coupled with a first end of the second substantially inelastic section 34, a second end of the second substantially inelastic section 34 may be coupled with a first end of the adjustable substantially inelastic section 40, a second end of the adjustable substantially inelastic section 40 may be coupled with a first end of the first substantially elastic section 36, a second end of the first substantially elastic section 36 may be coupled with the second end of the first substantially inelastic section 32. Thus, the strap 12 may comprise five portions that are stitched or removably coupled to adjacent portions to form a single, continuous strap 12 that may be worn around a user's torso. Any combination of stitching and removable coupling between portions of strap 12 are envisioned. For example, each end of the first substantially elastic section 36 may be stitched to the adjustable substantially inelastic section 40 and the first substantially inelastic section 32, while the adjustable substantially inelastic section 40 may be removably coupled to the second substantially inelastic section 34.

Figure 4:
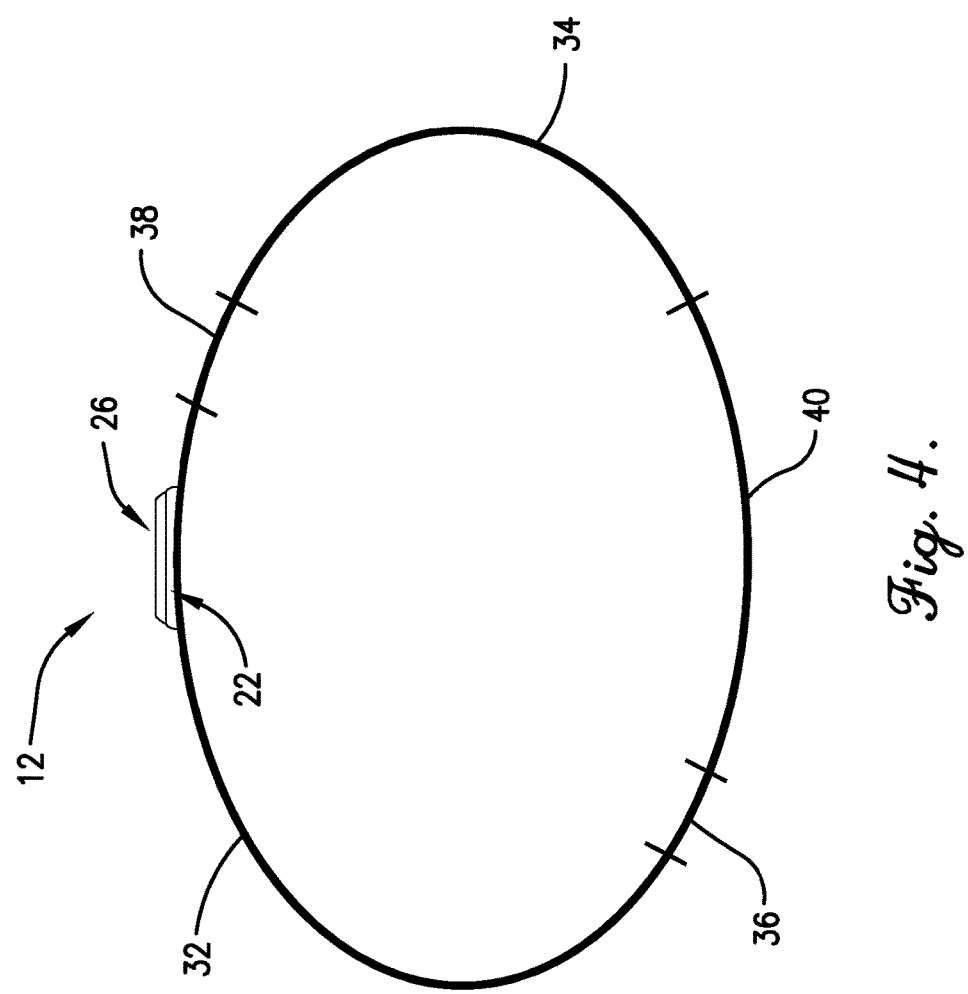
FIG. 4 is a schematic view of the first embodiment of the strap.

Typically, the electronics module 26 is positioned at a location along strap 12 such that the electronics module 26 is centered at the user's sternum (i.e., above the navel) and the first electrode 14 contacts the user's skin on one side of the sternum and the second electrode 16 contacts the user's skin on the other side of the sternum. In various embodiments, the lengths of each portion of the strap 12 may be determined such that portion of the strap 12 near the user's sternum and electrodes is substantially inelastic and the portions that are elastic or adjustable are positioned at other locations. For example, an elastic portion of the strap 12, such as the first or second substantially elastic sections 36, 38, may be offset to the right or left side of the user's sternum and the adjustable substantially inelastic section 40 may be positioned near the back of the strap 12 when worn by a user. The elastic portions of the strap 12 may be offset from the sternum, which is typically the position of the electronics module 26, and the center of the user's back because water tends to flow through the natural channels formed by these portions of the body. Consequently, in embodiments, lengths of each portion of strap 12 may be determined such that an inelastic portion of the band 12 is positioned at the user's sternum and center of his back. As shown in FIGS. 1-4, the first substantially inelastic section 32 may be positioned near the sternum and the adjustable substantially inelastic section 40 may be positioned near the center of the user's back approximately 180° apart from each other. Similarly, in embodiments of the strap 12 having two elastic portions, the centers of the first and second substantially elastic sections 36, 38 may be positioned approximately 180° apart from each other, as shown in FIG. 4. With this configuration, the second substantially elastic section 38 may be positioned along the right side of the user's chest, while the first substantially elastic section 36 may be positioned along the left side of the user's back to provide for increased range of movement at the side and back portions of strap 12 when worn by the user.

In embodiments, when the strap 12 is worn, the first substantially inelastic section 32 may cover at least a center portion of the user's chest and at least a portion of the user's left side and the second substantially inelastic section 34 may cover at least a portion of the user's right side and a portion of the user's back, while the adjustable substantially inelastic section 40 may cover a portion of the user's back. In other configurations, the first and second electrodes 14, 16 may be positioned closer together or otherwise arranged so that both electrodes 14, 16 contact the user's skin on the left side of the sternum.

The strap 12 may also possess the following characteristics. The strap 12 may have a total length that is capable of expanding only a limited amount when worn by a user. For example, the first and second substantially elastic sections 36, 38 and the first and second substantially inelastic sections 32, 34 may enable strap 12 to expand no more than one-quarter of the unstretched lengths of each section when the strap 12 is worn. This limited elongation of the strap 12 may able the strap 12 to stay in position on a user's chest during water activities such that the first and second electrode remain in contact with the user's skin and continue to provide an electronic heart signal. Conventional straps having significant elastic sections expand significantly. For example, the total length of some predominantly-elastic, conventional straps may expand to more than double their original, unstretched length, which may cause the conventional straps to rotate, roll, buckle, or fold over while the user is swimming.

In embodiments, a ratio of the sum of lengths of the first and second substantially inelastic sections 32, 34 to the sum of lengths of the first and second substantially elastic sections 36, 38 may be greater than 2:1 for all possible lengths and adjustment configurations of strap 12. Furthermore, the total length of the first and second substantially inelastic sections 32, 34 and the first and second substantially elastic sections 36, 38 when the strap 12 is stretched may be less than 1.15 times the total length of the sections 32, 34, 36, 38 when the strap 12 is unstretched, at typical deployment tensions. In other words, stretching the strap 12 may add less than 15% to the length of the first and second substantially inelastic sections 32, 34 and the first and second substantially elastic sections 36, 38.

Figure 7:
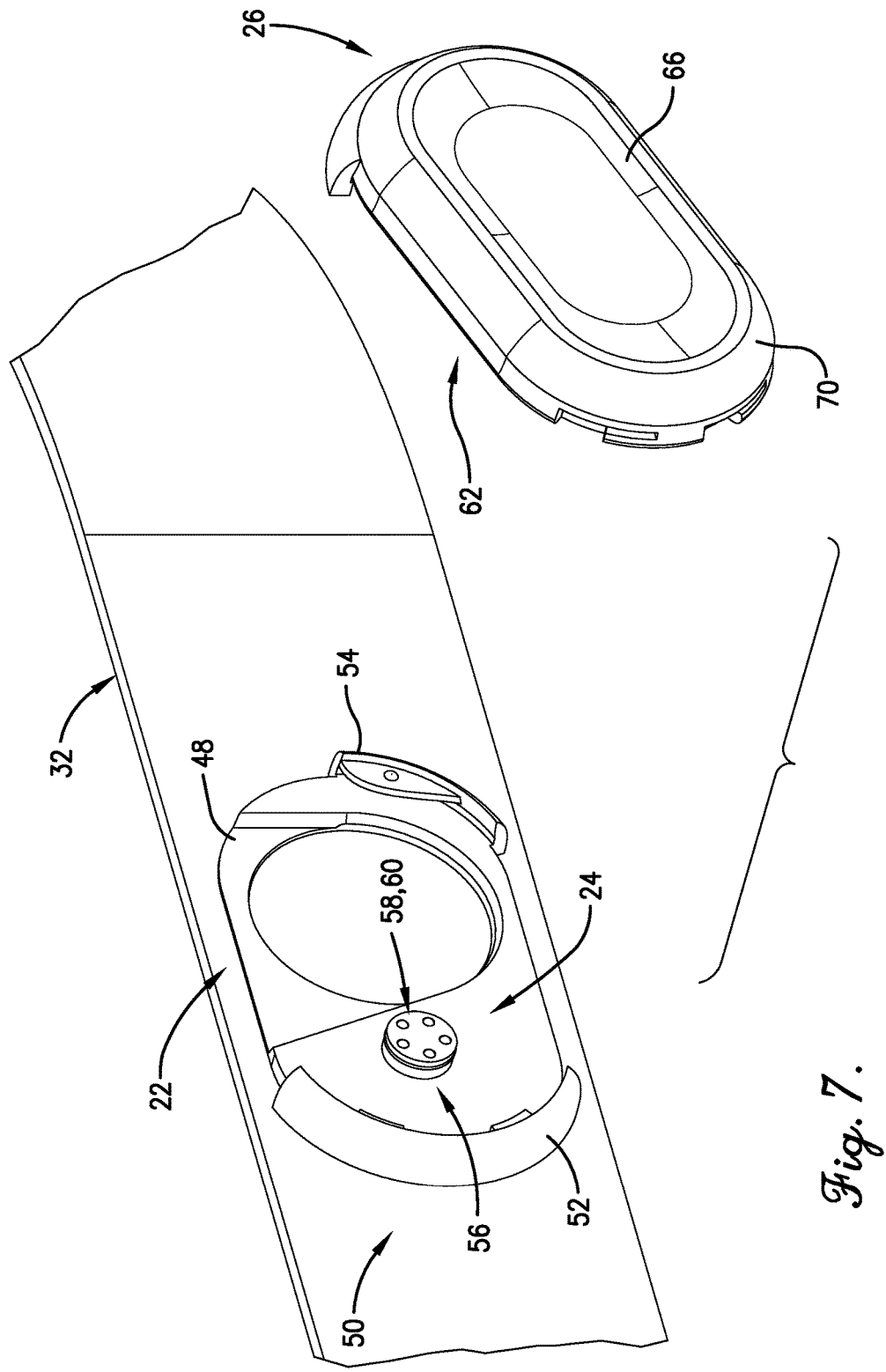
FIG. 7 is a fragmentary front perspective view from a second side of the module coupler, the first electronics module, and the electronics module.

The module coupler 22, as seen in FIGS. 1, 3, 5-8, 10, and 12-14, removably retains the electronics module 26 on the strap 12 and may include a base 48 and one or more sidewalls 50. As shown in FIG. 7, the base 48 may include a lower surface rigidly attached to the outer surface of the first substantially inelastic section 32 of the strap 12 and an opposing upper surface. In various embodiments, the base 48 may also include contours, cutouts, openings, or similar features. The sidewalls 50 extend upward from the base 48 and may include mating features that interact with similar features of the electronics module 26 to retain the electronics module 26 to the module coupler 22 in an interlocking manner, as seen in FIG. 13. For example, a first sidewall 52 at one end of the base 48 may include a couple of tabs protruding inward, while a second sidewall 54 at an opposing end may include a single tab protruding inward.

The first electrical connector 24, as seen in FIGS. 6, 7, 12, and 14, generally is in electrical contact with the first and second electrodes 14, 16 and may be positioned on the upper surface of the base 48 of the module coupler 22 and may include a post 56, a first contact 58, and a second contact 60. The post 56 may have an exemplary cylindrical shape and may be attached to the base 48. The post 56 may include mating features that interact with counterpart features of the electronics module 26 to secure the electronics module to the post 56 in an interlocking manner. The first and second contacts 58, 60 may each include a pin that is formed from electrically conductive material, such as stainless steel or copper. The first and second contacts 58, 60 may each also be enclosed by the post 56. In addition, the first and second contacts 58, 60 may extend from the lower surface of the base 48 to the top of the post 56 and may protrude therefrom.

The first contact 58 may be connected to the first electrode conductor 18, and the second contact 60 may be connected to the second electrode conductor 20. There may be one or more openings in the first substantially inelastic section 32 that allow the first and second electrode conductors 18, 20 to pass from the inner surface to the outer surface to connect to the first and second contacts 58, 60 at the lower surface of the base 48.

In some embodiments, the first contact 58 and the second contact 60 may each include a plurality of individual contacts. Generally, the number of first contacts 58 corresponds to the number of first electrode conductors 18, 20, which, in turn, corresponds to the number of first electrodes 14 positioned along the inner surface of strap 12 to sense the user's heart rate. And, the number of second contacts 60 corresponds to the number of second electrode conductors 18, 20, which, in turn, corresponds to the number of second electrodes 16 that are also positioned along the inner surface of strap 12 to sense the user's heart rate. However, in some embodiments, the number of first contacts 58 and the number of second contacts 60 may exceed the number of electrical conductors 18, 20 to facilitate transfer heart signals as well other signals (e.g., power, data, etc.).

In some embodiments, the strap 12 includes sensors other than the skin electrodes 14, 16. For example, strap 12 may include one or more portions that will change properties in response to being stretched in order to calculate a respiration rate for the user. In embodiments, the lengths of strap 12 and any portion thereof based on the extent a portion having a sensor is stretched. In one embodiment, strap 12 may include smart fabrics that change resistance with the varying amount of stretch or stretch force in one or more portions. The first contacts 58 and second contacts 60 may be used to facilitate measurement of the changing resistance and conductors, in addition to electrode conductors 18, 20, may be utilized.

In one embodiment, strap 12 includes electrodes other than the heart signal skin electrodes 14, 16. For example, additional electrodes may be utilized to measure galvanic skin response (GSR), also known as skin conductance, and one or more conductors in addition to electrode conductors 18, 20 may be utilized with strap 12. GSR may be measured to determine the level of a user's hydration, in particular when the user is using the strap 12 in dry conditions. One or more additional first contacts 58 and second contacts 60 may be used to facilitate measurement of GSR. However, in some configurations, GSR measurement may be performed through first and second electrodes 14, 16 used to provide a heart signal.

In embodiments, skin impedance and/or conductance may be determined using the heart signal provided by first and second electrodes 14, 16, or additional electrodes to allow for improvement of the heart signal through post-processing by the electronics module 26. Various techniques may be employed that utilize the determined skin impedance to identify and remove motion artifact noise from the heart signal provided by first and second electrodes 14, 16. For example, adaptive filtering techniques, such as the Least-Means Square (LMS) algorithm, may be employed for noise removal from the heart signal provided by first and second electrodes 14, 16.

In embodiments, the determined skin impedance and/or conductance is used to calculate a respiration rate for the user. This measurement may be made using the heart signal provided by first and second electrodes 14, 16, with the addition of one or more electrodes, conductors 18, 20, or first contacts 58 and second contacts 60. Skin impedance and/or conductance may be determined in dry conditions.

The electronics module 26, as seen in FIGS. 1, 3, 5-14, and 17, generally retains the electronic components that process the heart signal generated by the first and second electrodes 14, 16. The electronic components may include signal amplifiers, processing elements, memory elements, and the like which process the signal and determine the user's heart rate. In addition, the electronics module 26 may include wireless communication components such as transmitters, receivers, and antennas to wirelessly communicate heart rate information to external devices. Some of these components may be disposed on a printed circuit board. Furthermore, a battery or similar electrical power source may be retained within the electronics module 26.

In embodiments, the electronics module 26 may include one or more inertial sensors, such as one or more accelerometers or gyroscopes. Electronics module 26 may apply post-processing techniques to improve the quality of heart signal and accuracy of information determined using the heart signal by using signals generated by the inertial sensors. Various techniques may be employed which utilize the inertial measurement to identify and remove motion artifact noise from the heart signal. For example, adaptive filtering techniques, such as the Least-Means Square (LMS) algorithm, may be employed for noise removal from the heart signal provided by first and second electrodes 14, 16.

The electronics module 26 may include hardware provisions for selection of different configurations for analog processing of the heart signal provided by first and second electrodes 14, 16. For example, the electronics module 26 may be operable to change an amplification factor applied to the incoming heart signal. In embodiments, the electronics module 26 may be operable to change the amplification factor in response to signal attenuation, which may be caused by water interfering with the heart signal by entering and forming a conductive path between the first and second contacts of the electrical connectors when the electronics module is attached to the strap. Thus, the electronics module 26 may accommodate changing signal properties due to, for example, partial signal degradation due to water ingress.

The electronics module 26 may include a housing 62, as best seen in FIGS. 6-14, with at least an upper wall 66 that is generally accessible when the electronics module 26 is connected to strap 12 and a lower wall 64 having a second electrical connector 28 that is not accessible when the electronics module 26 is connected to strap 12. In exemplary embodiments, the housing 62 may be roughly oval or elliptical shaped and may include a rounded lower sidewall 68 attached to the perimeter of the lower wall 64 and a rounded upper sidewall 70 attached to the perimeter of the upper wall 66. Alternatively, the housing 62 may have a different shape with other sidewalls. The lower sidewall 68 may include mating features that interact with similar features of the module coupler 22 to retain the electronics module 26 to the module coupler 22, as seen in FIG. 13. In various embodiments, the housing 62 may further include a battery cover 72 or door that removably attaches to the lower wall 64 to retain the battery.

Figure 8:
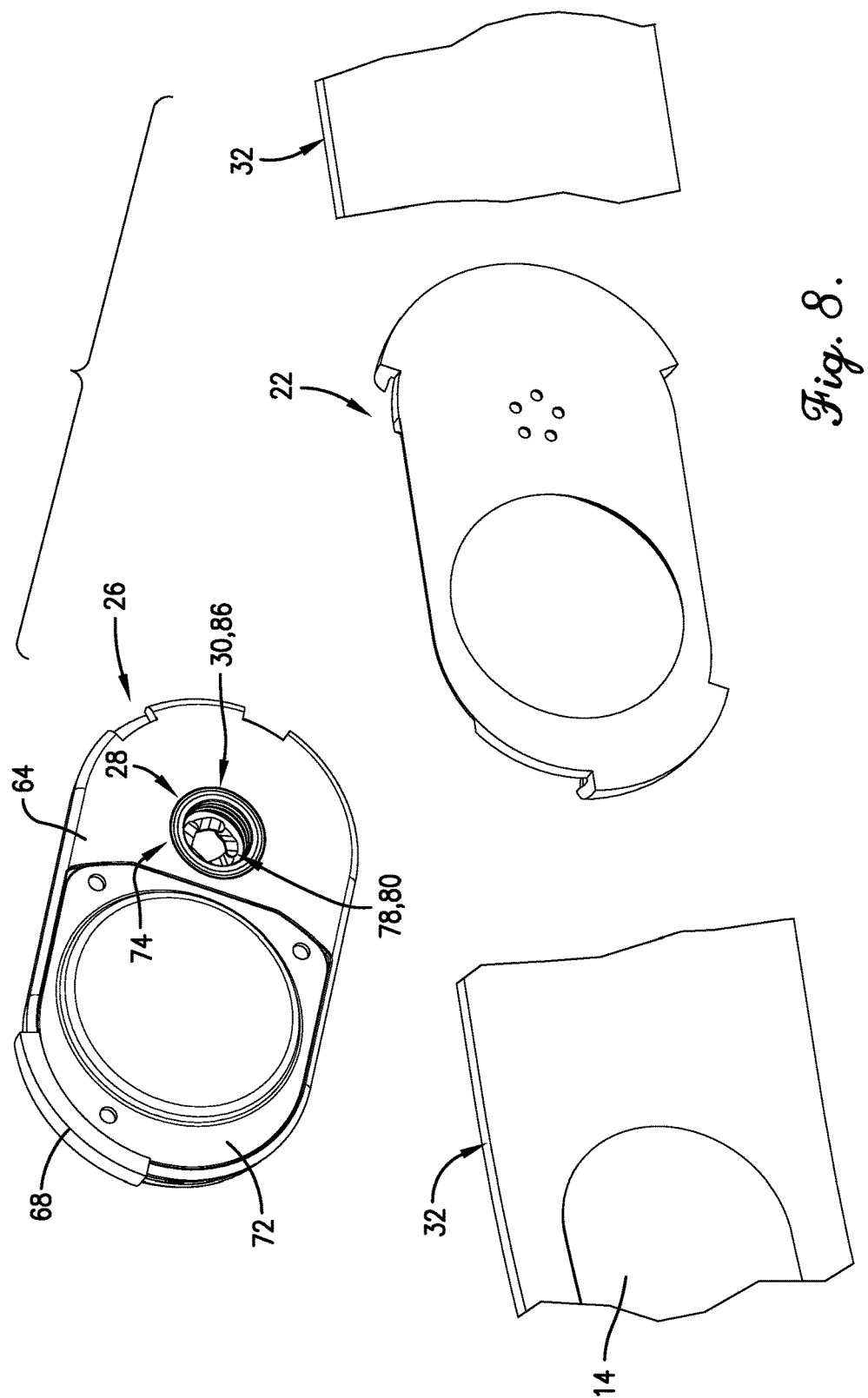
FIG. 8 is a fragmentary exploded view of the module coupler and the electronics module, further depicting a second electrical connector.
Figure 9:
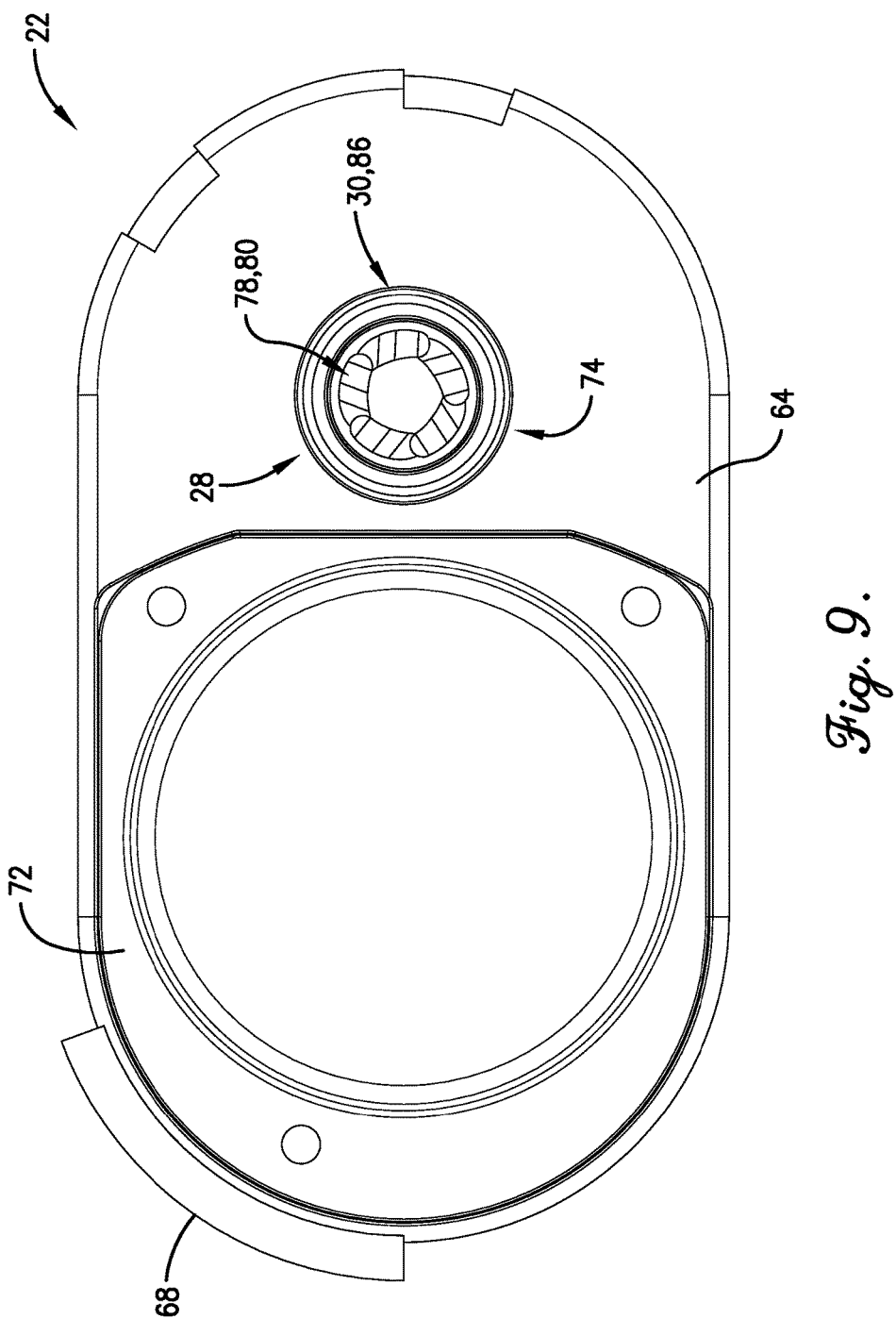
FIG. 9 is a bottom view of the electronics module including the second electrical connector.

The lower wall 64 may include at least one opening 74 that permits access to the second electrical connector 28 within the electronics module 26, as best seen in FIGS. 8 and 9. Aligned with the opening 74 may be a cylindrical sidewall 76, extending upward from the lower wall 64 to the interior of the housing 62. The opening 74 and the sidewall 76 are of a larger diameter than the post 56 of the module coupler 22 and may be configured to receive and surround the post 56 when the electronics module 26 is coupled to the module coupler 22.

The second electrical connector 28, as seen in FIGS. 8, 9, 12, and 14, generally provides electrical connection to the electronic components of the electronics module 26 and may be positioned in the housing 62. The second electrical connector 28 may include a first contact 78 and a second contact 80. In an exemplary embodiment, the first and second contacts 78, 80 may be disposed on the printed circuit board of the electronics module 26, typically via a solder connection. In other embodiments, the first and second contacts 78, 80 may be positioned elsewhere in or on the housing 62. Furthermore, exemplary embodiments of the first and second contacts 78, 80 may include electrically conductive leaf springs, typically formed from copper, stainless steel, or the like. In certain embodiments, the first contact 78 and the second contact 80 may each include a plurality of individual contacts. Generally, the number of first contacts 78 corresponds to the number of first contacts 58 of the first electrical connector 24. And, the number of second contacts 80 corresponds to the number of second contacts 60.

The water sealing feature 30, as seen in FIGS. 8, 9, and 14, generally prevents water from interfering with the electronic heart signal between the first electrical connector 24 and the second electrical connector 28 when the electronics module 26 is attached to the strap. The water sealing feature 30 may prevent water from accessing the electrical connectors 24, 28 when the electronics module 26 is attached to the module coupler 22, as described below. In a first embodiment shown in FIG. 14, the water sealing feature 30 may include water seals 82 which are formed from water proof or water resistant materials that are also durable, such as rubbers, elastomers, or the like. An exemplary water seal 82 may include an O-ring. In embodiments, the water seals 82 are integrated with the second electrical connector 28 on the lower wall 64 of the electronics module 26. The sidewall 76 may include one or more grooves 84, or recesses, axially-spaced along the inner surface thereof that receive and retain the water seals 82. In an exemplary configuration, the sidewall 76 may include two grooves 84, each receiving and retaining one O-ring shaped water seal 82, such that there are two o-ring seals that prevent water from interfering with the electronic heart signal between the first electrical connector 24 and the second electrical connector 28 when the electronics module 26 is attached to the strap.

In a second embodiment shown in FIGS. 8, 9, and 12, the water sealing feature 30 may include a water seal 86, which may also be formed from water proof or water resistant materials that are also durable, such as rubbers, elastomers, or the like. The water seal 86 may be generally cylindrical shaped with a circumferential sidewall 88, an upper collar 90, and a lower flange 92. The upper collar 90 may be coupled to one end of the sidewall 88 and may extend radially outward therefrom and curve or bend downward. The lower flange 92 may be coupled to the other end of the sidewall 88 and may extend radially outward therefrom. The water seal 86 may be integrated with the electronics module 26 and may be coupled to the sidewall 76 such that the upper edge of the sidewall 76 fits within the upper collar 90 and the lower flange 92 fits within a recess along the opening 74 of the lower wall 64. Thus, the water seal 86 may be firmly retained by the sidewall 76.

The electronics module 26 may attach to the module coupler 22 as follows. The electronics module 26 may be held above the module coupler 22 such that the opening 74 of the lower wall 64 is aligned with the post 56 of the first electrical connector 24. The electronics module 26 may be oriented such that the lower wall 64 is roughly parallel to the base 48 of the module coupler 22 and that the longitudinal axis of the electronics module 26 is at angle to the longitudinal axis of the module coupler 22. The electronics module 26 may be placed on the module coupler 22 such that the post 56 fits into the opening 74, as seen in FIG. 10. At this point, the first and second contacts 78, 80 of the second electrical connector 28 may be axially misaligned with the first and second contacts 58, 60, respectively, of the first electrical connector 24. The electronics module 26 may then be rotated so that the mating features of the electronics module 26 mate with the mating features of the module coupler 22 in order for the electronics module 26 to be securely retained on the module coupler 22. After the rotation of the electronics module 26, the first and second contacts 78, 80 of the second electrical connector 28 may be axially aligned with the first and second contacts 58, 60, respectively, of the first electrical connector 24 such that the first contact 78 of the electronics module 26 physically contacts or touches the first contact 58 of the module coupler 22, and the second contact 80 physically contacts the second contact 60.

When the electronics module 26 is securely attached to the module coupler 22, a watertight barrier is formed to prevent water from interfering with the electronic heart signal between the first electrical connector 24 and the second electrical connector 28 when the electronics module 26 is attached to the strap, as seen in FIGS. 12 and 14. Water being present between the first contact 58 and the second contact 60, the first contact 78 and the second contact 80, or a combination thereof may degrade or electrically short the electronic heart signal corresponding to the heartbeat of the user that is provided by the first and second electrodes 14, 16. Thus, a heart rate monitor 10 that is watertight enables the electronics module 26 to accurately determine the user's heart rate.

In some embodiments as shown in FIG. 14, the watertight barrier may be provided by the water seals 82. When the electronics module 26 is attached to the module coupler 22, the water seals 82, positioned in recesses on the sidewall 76, are in secure contact with an outer surface of the post 56 of the first electrical connector 24, which blocks the path that water may take to access the electrical connection of the two electrical connectors 24, 28. In other embodiments as shown in FIG. 12, the watertight barrier may be provided by the water seal 86. With the electronics module 26 attached to the module coupler 22, an inner surface of the water seal 86 makes secure contact with an outer surface of the post 56 along the axial length thereof—which, like the water seals 82, also blocks the path that water may take to access the electrical connection of the two electrical connectors 24, 28.

In an alternative embodiment of the interface of the first electrical connector 24 and the second electrical connector 28, the first contact 58 and the second contact 60 may be positioned as seen in FIG. 18. The first contact 78 and the second contact 80 may be positioned to align with the first contact 58 and the second contact 60, respectively. A plurality of water seals 94 may be utilized such that a water seal 94 may surround or enclose each of the first contact 58 and the second contact 60, the first contact 78 and the second contact 80, or combinations of both. The water seal 94 may be similar in structure to the water seal 82 or the water seal 86. When the electronics module 26 is attached to the module coupler 22, a watertight barrier may be formed by each of the water seals 94 surrounding the connection of the first contact 58 and the first contact 78 and the connection of the second contact 60 and the second contact 80.

Figure 20:
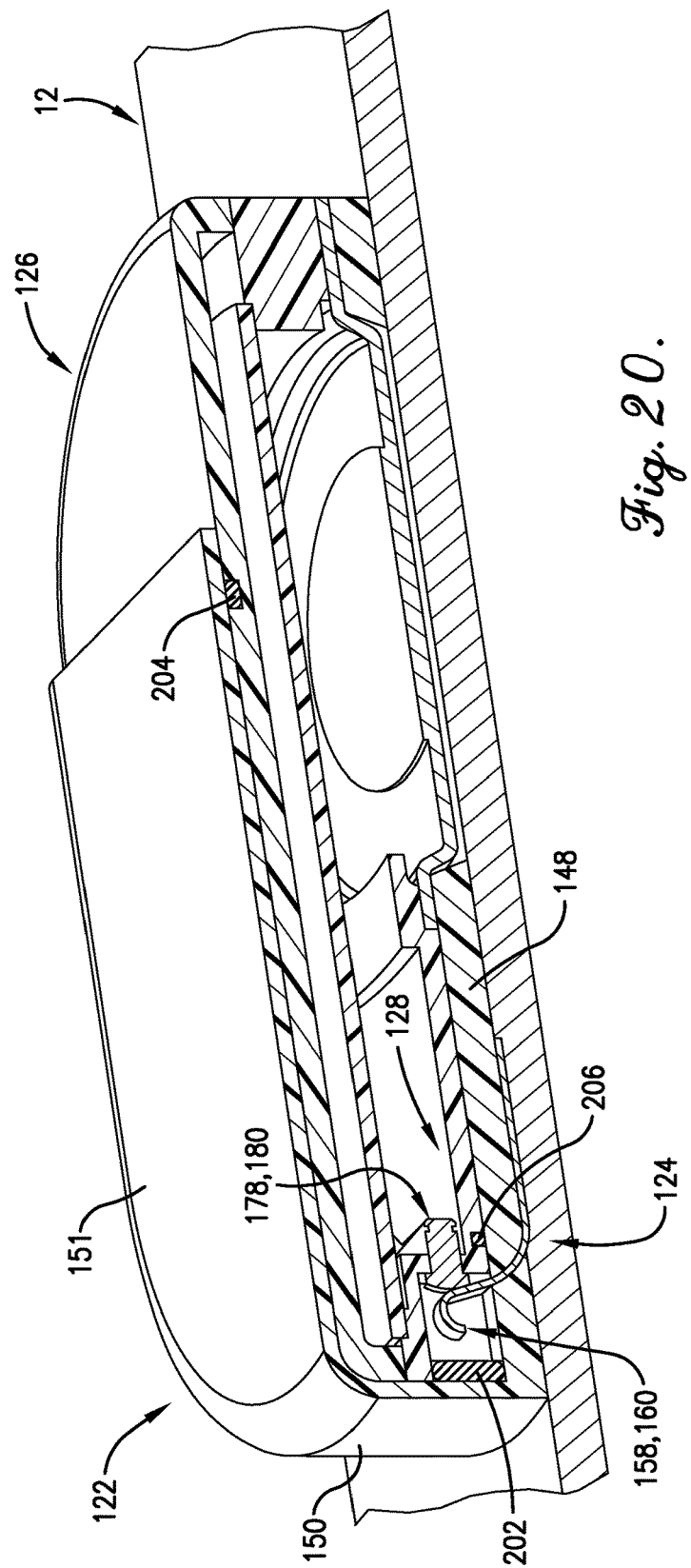
FIG. 20 is a sectional view of the second embodiment of the electronics module and a second embodiment of the module coupler.

Another embodiment of a module coupler 122 may include a base 148, a sidewall 150, and an upper wall 151, as shown in FIG. 20. The base 148 may be similar to the base 48 and may have a roughly oval or elliptical shape. The sidewall 150 may couple to a first end of the base 148 and to opposing sides of the base 148 extending greater than half the length of the sides. The upper wall 151 may couple to the sidewall 150, having the same length thereof. Thus, the upper wall 151 and the sidewall 150 may form an opening at one end of the module coupler 122. The module coupler 122 may further include a first water seal 202 positioned along an inner surface of the sidewall 150, where the sidewall 150 connects to the base 148.

Another embodiment of a first electrical connector 124, as shown in part in FIG. 20, may include a plurality of first contacts 158 and a plurality of second contacts 160. Each first contact 158 and each second contact 160 may include an elongated strip of electrically conductive material, such as metal, with a first end and an opposing second end. The first ends of the first and second contacts 158, 160 may be embedded in the first substantially inelastic section 32 of the strap 12 and may connect to the first and second electrode conductors 18, 20. The second ends of the first and second contacts 158, 160 may extend upward from the base 148 and may curve over along the length. Hence, a middle portion of the first and second contacts 158, 160 may pass through the base 148.

Figure 19:
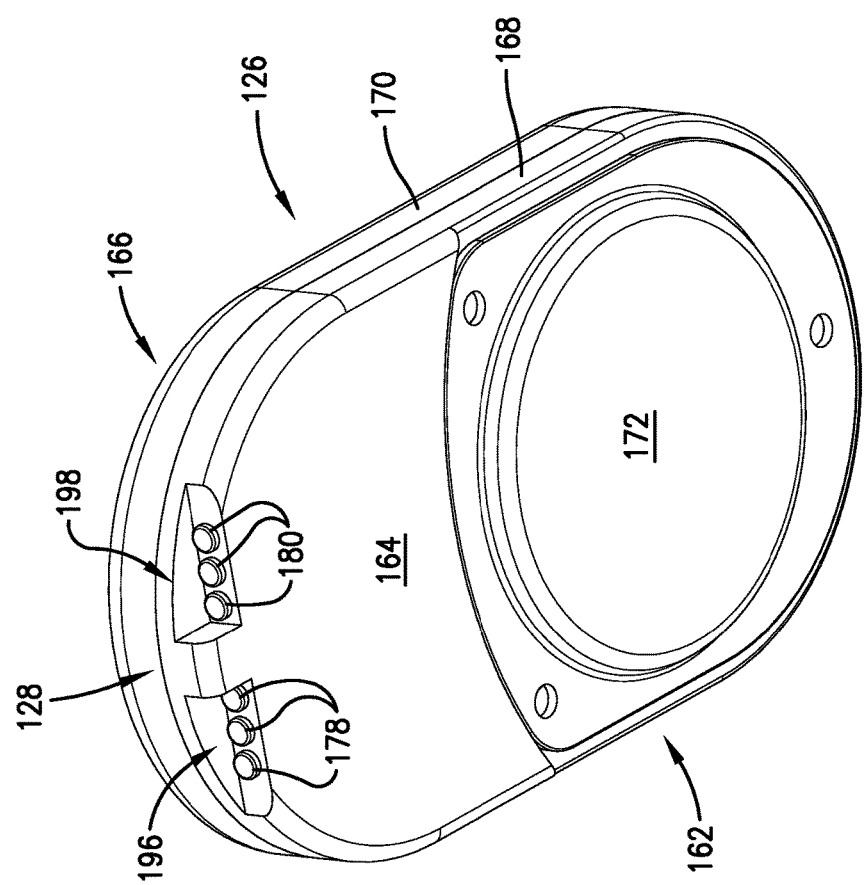
FIG. 19 is a lower perspective view of a second embodiment of the electronics module.

Another embodiment of an electronics module 126, as shown in FIGS. 19 and 20, may include a housing 162 with a lower wall 164, an upper wall 166, a lower sidewall 168, an upper sidewall 170, and a battery cover 172, which all may be similar to the like-named components of the electronics module 26, with the following exceptions. A first recess 196 and a second recess 198 may be formed in the lower wall 164 and the lower sidewall 150 at a first end of each. The first recess 196 may be positioned on a left side of the electronics module 126, while the second recess 198 may be positioned on a right side of the electronics module 126. The electronics module 126 may further include a second water seal 204 positioned along the width of the upper wall 151 and a third water seal 206 positioned along the lower wall 164 adjacent to the first recess 196 and the second recess 198.

Another embodiment of a second electrical connector 128, as shown in FIGS. 19 and 20, may include a plurality of first contacts 178 and a plurality of second contacts 180. Each first contact 178 and each second contact 180 may include a cylindrical pin with a first end that protrudes from the lower sidewall 150. The first ends of the first contacts 178 may extend into the first recess 196. The first ends of the second contacts 180 may extend into the second recess 198. The pin of each first contact 178 and each second contact 180 may have an opposing second end that connects to a printed circuit board which retains the electronic components of the electronics module 126.

The electronics module 126 may attach to the module coupler 122 as follows. The first end of the electronics module 126 may be inserted into the opening of the module coupler 122 between the upper wall 151 and the base 148. For instance, the first end of the electronics module 126 may slide along a top surface of module coupler 122 until an interlocking element of the electronics module 126 couples with a counterpart interlocking element of the module coupler 122. The second electrical connector 128 may advance toward the first electrical connector 124 until the first and second contacts 178, 180 press on the first and second contacts 158, 160, respectively. When the electronics module 126 is fully inserted into the module coupler 122, the first water seal 202 may form a seal between the sidewall 150 of the module coupler 122 and the upper sidewall 150 of the electronics module 126. The third water seal 206 may form a seal between the base 148 of the module coupler 122 and the lower wall 164 of the electronics module 126. The second water seal 204 may form a seal between the upper wall 151 of the module coupler 122 and the upper wall 166 of the electronics module 126.

Although the technology has been described with reference to the embodiments illustrated in the attached drawing figures, it is noted that equivalents may be employed and substitutions made herein without departing from the scope of the technology as recited in the claims.

Having thus described various embodiments of the technology, what is claimed as new and desired to be protected by Letters Patent includes the following:

What is claimed is:

1. A chest-worn strap for use with a swimming heart rate electronics module, the strap comprising:
   a first substantially elastic section and a second substantially elastic section each configured to stretch when the strap is worn, the combination of the first and the second substantially elastic sections having a first length;
   a first substantially inelastic section and a second substantially inelastic section, the first substantially inelastic section separating the first and the second substantially elastic sections and positioned at least partially in a front portion of the strap and configured to cover at least a portion of a user's chest when the user is engaged in a water activity, the first and second substantially inelastic sections having a combined second length at least twice the first length;

a first electrode and a second electrode spaced apart from one another and positioned on an inner surface of the first substantially inelastic section, the electrodes configured to contact the user's skin and provide an electronic heart signal corresponding to the heartbeat of the user;

wherein a center of the first substantially elastic section and a center of the second substantially elastic section are spaced approximately 180 degrees apart along a circumference of the strap.

2. The strap of claim 1, wherein the second substantially inelastic section comprises an adjustable substantially inelastic section positioned in a back portion of the strap configured to adjust a total length of the strap.

3. The strap of claim 1, wherein the combination of the first and the second substantially elastic sections stretches to a maximum third length that is larger than the first length and does not increase as the total length of the strap increases.

4. The strap of claim 1, wherein the first substantially inelastic section positioned at least partially in a front portion of the strap covers the first and second electrodes and the user's sternum.

5. The strap of claim 4, wherein the first substantially elastic section is offset to one side of the strap.

6. The strap of claim 1, further comprising an electrical connector positioned on an outer surface of the first substantially inelastic section and in electronic contact with the first and second electrodes.

7. The strap of claim 6, wherein the electrical connector is enclosed by a water sealing feature that includes first and second O-rings axially spaced and positioned on a post of the electrical connector.

8. The strap of claim 6, wherein the electrical connector is enclosed by a water sealing feature that includes a cylindrical shaped water seal with a circumferential sidewall, an upper collar, and a lower flange.

9. The strap of claim 6, further comprising a module coupler on an outer surface of the strap that attaches to an electronics module, wherein the electrical connector is enclosed by a water sealing feature that includes a plurality of seals between the module coupler and the electronics module.

10. The strap of claim 1, wherein the first and second substantially inelastic sections are coated along an inner surface with a material to increase a coefficient of static friction between the strap and the user's skin.

11. A swimming heart rate monitor comprising:
a strap configured to cover at least a portion of a user's chest having a first substantially elastic section, a second substantially elastic section, a first substantially inelastic section separating the first and the second substantially elastic sections and positioned at least partially in a front portion of the strap and configured to cover at least a portion of a user's chest when the user is engaged in a water activity, and a second substantially inelastic section, the strap having a total length that is capable of expanding no more than one-quarter of the unstretched length for all possible lengths of the strap when the strap is worn;

a first electrode and a second electrode spaced apart from one another and positioned on an inner surface of the strap, the electrodes configured to contact the user's skin and provide an electronic heart signal corresponding to the heartbeat of the user;

a first electrical connector positioned on an outer surface of the strap and in electronic communication with the first and second electrodes;

an electronics module configured to removably attach to the strap and to process the heart signal, the electronics module including a housing with an upper wall and an opposing lower wall;

a second electrical connector accessed on the lower wall of the electronics module housing and configured to electrically connect to the first electrical connector; and a water sealing feature that prevents water from interfering with the electronic heart signal between the first electrical connector and the second electrical connector when the electronics module is attached to the strap and submerged in water;

wherein a center of the first substantially elastic section and a center of the second substantially elastic section are spaced approximately 180 degrees apart along a circumference of the strap.

12. The swimming heart rate monitor of claim 11, wherein the first electrical connector includes a post that encloses a plurality of electrical contacts and the second electrical connector includes a plurality of contacts that are accessed through an opening in the lower wall of the electronics module housing.

13. The swimming heart rate monitor of claim 12, wherein the water sealing feature includes a cylindrical water seal retained in the opening of the lower wall of the electronics module housing, such that the water seal contacts an outer surface of the post and forms a watertight barrier when the electronics module is attached to the strap.

14. The swimming heart rate monitor of claim 12, wherein the water sealing feature includes first and second O-rings axially spaced and positioned on the post, such that the O-rings contact an inner surface of the opening of the lower wall and form a watertight barrier when the electronics module is attached to the strap.

15. The swimming heart rate monitor of claim 12, wherein each electrical contact of the first electrical connector includes an elongated pin and each electrical contact of the second electrical connector includes a leaf spring configured to receive a corresponding pin of the first electrical connector.

16. The swimming heart rate monitor of claim 11, further comprising a module coupler on an outer surface of the strap that attaches to the electronics module, wherein the water sealing feature includes a plurality of seals between the module coupler and the electronics module, such that the plurality of seals contact an outer surface of the electronics module and form a watertight barrier when the electronics module is attached to the strap.

17. A swimming heart rate monitor comprising:
a strap including a substantially first inelastic section configured to cover at least a front portion of a user's chest when the user is engaged in a water activity, a second substantially inelastic section, a first substantially elastic section, and a second substantially elastic section, the combination of the first and the second substantially elastic sections configured to stretch when the strap is worn and separated by the first substantially inelastic section;

a first electrode and a second electrode spaced apart from one another and positioned on an inner surface of the first substantially inelastic section, the electrodes configured to contact the user's skin and provide an electronic heart signal corresponding to the heartbeat of the user;

a module coupler positioned on an outer surface of the strap, the module coupler including a first mating feature;

a first electrical connector in electrical contact with the first and second electrodes and retained on the module coupler, the first electrical connector including a post that encloses a plurality of electrical contacts;

an electronics module configured to process the heart signal, the electronics module including a housing with an upper wall and an opposing lower wall, the housing including a second mating feature configured to mate with the first mating feature to retain the electronics module to the module coupler;

a second electrical connector configured to electrically connect to the first electrical connector, the second electrical connector including a plurality of contacts that are accessed through an opening in the lower wall of the electronics module housing; and a water sealing feature that prevents water from interfering with the electronic heart signal between the first electrical connector and the second electrical connector when the electronics module is attached to the module coupler and submerged in water;

wherein a center of the first substantially elastic section and a center of the second substantially elastic section spaced approximately 180 degrees apart along a circumference of the strap.

18. The swimming heart rate monitor of claim 17, wherein the water sealing feature includes a cylindrical water seal retained in the opening of the lower wall, such that the water seal contacts an outer surface of the post and forms a watertight barrier when the electronics module is attached to the strap.

19. The swimming heart rate monitor of claim 17, wherein the water sealing feature includes first and second O-rings axially spaced and positioned on the post, such that the O-rings contact an inner surface of the opening of the lower wall and form a watertight barrier when the electronics module is attached to the strap.

20. The swimming heart rate monitor of claim 17, wherein the second electrical connector accessed on the electronics module housing may electrically connect to an electrical connector of a strap used in dry conditions.

21. The strap of claim 11, wherein the second substantially inelastic section comprises an adjustable substantially inelastic section positioned in a back portion of the strap configured to adjust the total length of the strap.

22. The strap of claim 17, wherein the second substantially inelastic section comprises an adjustable substantially inelastic section positioned in a back portion of the strap configured to adjust a total length of the strap.

* * * * *